US012594019B2

(12) United States Patent (10) Patent No.: US 12,594,019 B2
Majumder et al. (45) Date of Patent: Apr. 7, 2026

(54) DETECTION OF ATRIAL TACHYCARDIA BASED ON REGULARITY OF CARDIAC RHYTHM

(71) Applicant: Medtronic, Inc., Minneapolis, MN (US)

(72) Inventors: Shubha Majumder, Minneapolis, MN (US); Sean R. Landman, Minneapolis, MN (US); Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 386 days.

(21) Appl. No.: 17/339,308

(22) Filed: Jun. 4, 2021

(65) Prior Publication Data

US 2022/0386930 A1 Dec. 8, 2022

(51) Int. Cl.
| | |
|---|---|
| *A61B 5/363* | (2021.01) |
| *A61B 5/00* | (2006.01) |
| *A61B 5/352* | (2021.01) |
| *A61B 5/353* | (2021.01) |
| *A61B 5/355* | (2021.01) |

(52) U.S. Cl.
CPC ............. *A61B 5/363* (2021.01); *A61B 5/352* (2021.01); *A61B 5/353* (2021.01); *A61B 5/355* (2021.01); *A61B 5/6802* (2013.01); *A61B 5/686* (2013.01)

(58) Field of Classification Search
CPC ...... A61N 1/3624; A61B 5/364; A61B 5/363; A61B 5/361; A61B 5/352
See application file for complete search history.

(56) References Cited

U.S. PATENT DOCUMENTS

| | | |
|---|---|---|
| 5,840,038 A | 11/1998 | Xue et al. |
| 6,230,059 B1 | 5/2001 | Duffin |
| 6,412,490 B1 | 7/2002 | Lee |
| 6,438,410 B2 | 8/2002 | Hsu et al. |
| 6,760,620 B2 | 7/2004 | Sippens Groenewegen |
| 6,766,190 B2 | 7/2004 | Ferek-Petric |
| 6,922,584 B2 | 7/2005 | Wang et al. |
| 6,980,860 B2 | 12/2005 | Stadler et al. |

(Continued)

OTHER PUBLICATIONS

Mehra et al., "Algorithms for Atrial Tachyarrhythmia Detection for Long-Term Monitoring with Implantable Devices," Chapter 8, Algorithms for Atrialtachyarrhythmia Detection, 40 pp.

(Continued)

*Primary Examiner* — George R Evanisko
(74) *Attorney, Agent, or Firm* — Shumaker & Sieffert, P.A.

(57) ABSTRACT

This disclosure is directed to systems and techniques for determining an evidence level of an atrial tachycardia (AT) episode based on heart beat intervals in the cardiac activity data over a pre-determined time period. Based on a determination that the evidence level indicates relatively regular heart beat intervals, the example techniques apply a first set of AT detection criteria and indicate a detection of an AT episode based on satisfaction of at least one of the first set of AT detection criteria. Based on a determination that the evidence level indicates relatively irregular heart beat intervals, the example techniques apply a second set of AT detection criteria and indicate a detection of an AT episode based on based on satisfaction of at least one of the second set of AT detection criteria.

11 Claims, 12 Drawing Sheets

(56) References Cited

U.S. PATENT DOCUMENTS

| | | | |
|---|---|---|---|
| 7,103,404 | B2 | 9/2006 | Stadler et al. |
| 7,146,213 | B1 | 12/2006 | Levine |
| 7,184,834 | B1 | 2/2007 | Levine |
| 7,783,354 | B2 | 8/2010 | Gunderson |
| 8,447,400 | B2 | 5/2013 | More et al. |
| 8,639,316 | B2 | 1/2014 | Sarkar |
| 8,750,973 | B2 | 6/2014 | Katz et al. |
| 9,138,590 | B2 | 9/2015 | Zhang et al. |
| 9,619,660 | B1 | 4/2017 | Felix et al. |
| 9,622,778 | B2 | 4/2017 | Wengreen et al. |
| 9,730,604 | B2 | 8/2017 | Li et al. |
| 9,802,056 | B2 | 10/2017 | Allavatam et al. |
| 10,575,748 | B2 | 3/2020 | Higgins et al. |
| 10,617,356 | B2 | 4/2020 | Wang et al. |
| 10,869,610 | B2 | 12/2020 | Lu et al. |
| 11,071,500 | B2 | 7/2021 | Cheng et al. |
| 11,283,161 | B2 | 3/2022 | Zhao |
| 11,400,298 | B2 | 8/2022 | Hoffman et al. |
| 11,779,370 | B2 | 10/2023 | Vanderpool et al. |
| 2005/0154421 | A1 | 7/2005 | Ousdigian |
| 2006/0247548 | A1* | 11/2006 | Sarkar .................... A61B 5/363 600/515 |
| 2012/0283705 | A1 | 11/2012 | Lee et al. |
| 2013/0296680 | A1 | 11/2013 | Linker et al. |
| 2014/0276928 | A1 | 9/2014 | Vanderpool et al. |
| 2017/0095173 | A1 | 4/2017 | Bar-tal et al. |
| 2020/0046245 | A1 | 2/2020 | Qu et al. |
| 2020/0108260 | A1 | 4/2020 | Haddad et al. |
| 2020/0229713 | A1 | 7/2020 | Gopalakrishnan et al. |
| 2020/0298002 | A1 | 9/2020 | Pikulenko et al. |
| 2020/0357517 | A1 | 11/2020 | Haddad et al. |
| 2020/0383597 | A1 | 12/2020 | Rajagopal et al. |
| 2020/0383702 | A1 | 12/2020 | Vanderpool et al. |
| 2021/0343416 | A1 | 11/2021 | Chakravarthy et al. |
| 2022/0023626 | A1 | 1/2022 | Haddad et al. |
| 2022/0039729 | A1 | 2/2022 | Fontanarava et al. |
| 2022/0384014 | A1 | 12/2022 | Sarkar et al. |

OTHER PUBLICATIONS

International Search Report and Written Opinion of International Application No. PCT/US2022/028459 dated Aug. 4, 2022, 12 pp.
Banchs, Javier, "Atrial Tachycardia: Diagnosis and Treatment", The Cardiology Advisor, Jun. 4, 2021, 29 pp.
Communication pursuant to Article 94(3) EPC from counterpart European Application No. 22726358.9 dated Apr. 9, 2025, 4 pp.
"Inventing AI Tracing the diffusion of artificial intelligence with U.S. patents", Office ofthe Chief Economist IP Data Highlights, vol. 5, Oct. 2020, 19 pp., Retrieved from the Internet on Aug. 8, 2025 from URL: https://www.uspto.gov/sites/default/files/documents/OCE-DH-AI.pdf.
"Scalogram Computation in Signal Analyzer", Mathworks, 4 pp., Retrieved from the Internet on Aug. 8, 2025 from URL: httpszllwww.mathworks.com/help/signal/ug/scalogram-computation-in-signal-analyzer.html.

Arrobo et al., "An Innovative Wireless Cardiac Rhythm Management (iCRM) System", Wireless Telecommunications Symposium, IEEE, Apr. 9, 2014, 5 pp.
Condon, "Medtronic CEO predicts AI, machine learning as 'the newfrontier for medtech'—4 key quotes", Becker's SpineReview, Jan. 11, 2021, 2 pp., URL: https://www.beckersspine.com/spinal-tech/medtronic-ceo-predicts-ai-machine-learning-as-the-new-frontier-for-medtech-4-key-quotes/.
Cookson, "Huge surge in AI patent applications in past 5 years", financial times, Jan. 31, 2019, 4 pp., URL: https://www.ft.com/content/d93866aa-247d-11e9-b329-c7e60eb5ffdf.
Halpern et al., "thepracticaldev/orly / full-res", Github, Dec. 19, 2016, 5 pp., Retrieved from the Internet on Aug. 8, 2025 from URL: https://github.com/thepracticaldev/orly-full-res.
Henry, "Patent Litigation Trends in Artificial Intelligence", Bloomberg Law, Dec. 29, 2020, 3 pp., URL: https://news.bloomberglaw.com/us-law-week/patent-litigation-trends-in-artificial-intelligence.
Knight, "Nine charts that really bring homejust how fast AI is growing", MIT Technology Review, Dec. 12, 2018, 6 pp., URL: https://www.technologyreview.com/2018/12/12/138682/data-that-illuminates-the-ai-boom/.
Savage, "Learning the algorithms of power", Artificial intelligence, vol. 588, Springer Nature Limited., Dec. 10, 2020, pp. 8102-8104.
Savage, "The race to the top among the world's leaders in artificial intelligence", Nature, Dec. 9, 2020, 3 pp., URL: https://www.naturecom/articles/d41586-020-03409-8; Only abstract available.
Smith et al., "Autocorrelation: What It Is, How It Works, Tests", Investopedia, Sep. 10, 2024, 5 pp., URL: https://www.investopedia.com/terms/a/autocorrelation.asp.
U.S. Appl. No. 19/124,999, filed Oct. 26, 2023, naming inventors Majumder et al.
U.S. Appl. No. 16/401,553, filed May 2, 2019, naming inventors Cheng et al.
U.S. Appl. No. 16/866,178, filed May 4, 2020, naming inventors Hoffman et al.
U.S. Appl. No. 29/748,593, filed Aug. 31, 2020, naming inventors Vanderpool et al.
U.S. Appl. No. 29/748,588, filed Aug. 31, 2020, naming inventors Vanderpool et al.
U.S. Appl. No. 17/165,304, filed Feb. 2, 2021, naming inventors Vanderpool et al.
U.S. Appl. No. 16/515,449, filed Jul. 18, 2019, naming inventor Zhao.
Sarkar et al., "A Detector for a Chronic Implantable Atrial Tachyarrhythmia Monitor", IEE Transactions on Biomedical Engineering, vol. 55, No. 3, Mar. 2008, 6 pp.
Lee et al., "Automatic Motion and Noise Artifact Detection in Holter ECG Data Using Empirical Mode Decomposition and Statistical Approaches," IEEE Transactions on Biomedical Engineering, vol. 59, No. 6, Jun. 2012, 8 pp.
"Atrial Tachycardia," Johns Hopkins Medicine, retrieved from https://www.hopkinsmedicine.org/healthIconditions-and-diseases/atrial-tachycardia on Jun. 4, 2021, 4 pp.

* cited by examiner

DETECTION OF ATRIAL TACHYCARDIA BASED ON REGULARITY OF CARDIAC RHYTHM

FIELD

The disclosure relates generally to medical systems and, more particularly, medical systems configured to monitor patient activity for changes in patient health.

BACKGROUND

Some types of medical systems may monitor various data (e.g., a cardiac electrogram (EGM) and activity) of a patient or a group of patients to detect changes in health. In some examples, the medical system may monitor the cardiac EGM to detect one or more types of arrhythmia, such as bradycardia, tachycardia (e.g., atrial tachycardia), fibrillation (e.g., atrial fibrillation), or asystole (e.g., caused by sinus pause or AV block). In some examples, the medical system may include one or more of an implantable medical device or a wearable device to collect various measurements used to detect changes in patient health.

SUMMARY

Medical systems and techniques as described herein detect atrial tachycardia (AT) for a patient based upon cardiac activity. An example medical system includes an example medical device executing an example technique for detecting an atrial tachycardia (AT) using an innovative dichotomy of criteria. The example technique determines characteristics of the cardiac activity, and selects an effective set of criteria to apply to the cardiac activity based on such characteristics. Certain characteristics dictate that a given set of criteria relate to a particular feature or metric of the cardiac activity, and thus different sets of criteria may be applied to the cardiac activity based on the determined characteristics.

A variety of medical devices (e.g., implantable devices, wearable devices, etc.) may be configured to monitor electrical signals from electrodes configured to sense cardiac activity and detect an AT episode by calibrating the detection algorithm to evidence of cardiac rhythm regularity/irregularity. Such a technique not only improves AT detection in general, but also reduces a false detection rate, and accomplishes complementary goals of lowering operational resource requirements and lowering overall resource utilization. Having a lower resource footprint enables smaller and less complex embodiments of these techniques (e.g., relatively small and low-power wearable or implantable monitors). A medical device equipped with substantial resource capacities is no longer needed; instead, a medical device with fewer capacities of processing, network, and storage resources can be configured to detect changes in patient health in accordance with any technique described herein. In view of the above, the present disclosure describes a technological improvement or a technical solution that is integrated into a practical application.

In one example, a medical system comprises: one or more sensors configured to sense cardiac activity of a patient; sensing circuitry configured to provide cardiac activity data based on the sensed cardiac activity; and processing circuitry configured to: determine an evidence level of an atrial tachycardia (AT) episode based on heart beat intervals in the cardiac activity data over a pre-determined time period, wherein the evidence level is computed from at least one regularity measure and at least one irregularity measure of the heart beat intervals; based on a determination that the evidence level indicates relatively regular heart beat intervals over the pre-determined time period: apply, to the cardiac activity data, a first set of AT detection criteria; and indicate a detection of an AT episode based on satisfaction of at least one of the first set of AT detection criteria; and based on a determination that the evidence level indicates relatively irregular heart beat intervals over the pre-determined time period: apply, to the cardiac activity data, a second set of AT detection criteria, the second set of AT detection criteria including at least one criterion different from the first set of AT detection criteria; and indicate a detection of an AT episode based on based on satisfaction of at least one of the second set of AT detection criteria.

In another example, a method comprises: generating, by sensing circuitry, cardiac activity data based on sensed cardiac activity; determining, by processing circuitry, an evidence level of an atrial tachycardia (AT) episode based on heart beat intervals in the cardiac activity data, wherein the evidence level is computed from at least one regularity measure and at least one irregularity measure of the heart beat intervals; based on a determination that the evidence level indicates relatively regular heart beat intervals, applying a first set of AT detection criteria to the cardiac activity data, and indicating a detection of an AT episode based on satisfaction of at least one of the first set of AT detection criteria; and based on a determination that the evidence level indicates relatively irregular heart beat intervals, applying a second set of AT detection criteria to the cardiac activity data, the second set of AT detection criteria including at least one criterion different from the first set of AT detection criteria, and indicating a detection of an AT episode based on satisfaction of at least one of the second set of AT detection criteria.

In another example, a non-transitory computer-readable storage medium comprising program instructions that, when executed by processing circuitry of a medical system, cause the processing circuitry to: determine an evidence level of an atrial tachycardia (AT) episode based on heart beat intervals in cardiac activity data, wherein the evidence level is computed from at least one regularity measure and at least one irregularity measure of the heart beat intervals; based on a determination that the evidence level indicates relatively regular heart beat intervals: apply, to the cardiac activity data, a first set of AT detection criteria; and indicate a detection of an AT episode based on satisfaction of at least one of the first set of AT detection criteria; and based on a determination that the evidence level indicates relatively irregular heart beat intervals: apply, to the cardiac activity data, a second set of AT detection criteria, the second set of AT detection criteria including at least one criterion different from the first set of AT detection criteria; and indicate a detection of an AT episode based on satisfaction of at least one of the second set of AT detection criteria.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

In general, medical systems according to this disclosure implement techniques for detecting an atrial tachycardia (AT) in a patient based on that patient's cardiac activity. An implantable or insertable medical device may be configured to record the patient's cardiac activity in some form and then, execute a detection analysis on that patient's cardiac activity data as described herein. In some examples, by restricting the detection analysis to features that are well-suited for regularity level or irregularity level of the patient's cardiac activity, the detection analysis is capable of distinguishing AT episodes from non-AT episodes and avoiding detection of false AT episodes. The present disclosure describes how the detection analysis achieves a considerable level of accuracy (e.g., in terms of sensitivity and specificity). The medical device makes advantageous use of the detection analysis described herein to provide accurate detections of true AT episodes. The medical device may achieve substantially high sensitivity and specificity metric scores to the extent that clinicians may use the medical device for monitoring the patient for AT episodes.

Hence, the techniques described in the present disclosure may add an AT detection feature to any given medical device or further improve upon any given medical device's AT detection feature with enhanced (e.g., more accurate) functionality. In some instances, that improvement may open a new application for legacy medical devices by rendering the legacy medical device's AT detection functionality more clinically beneficial. In addition, medical devices, in general, may leverage the techniques described herein to reduce resource costs.

Example medical devices that may collect patient cardiac activity data may include an implantable or wearable monitoring device, such as the Reveal LINQ™ Insertable Cardiac Monitor (ICM), Medtronic, Inc. of Minneapolis, MN, a pacemaker/defibrillator, or a ventricular assist device (VAD).

The example medical device may communicate the patient cardiac activity data to other devices, such as a computing device, and those devices may further analyze the patient cardiac activity data and then, provide a report regarding the patient's activities and health. The report may compare various implementations of the techniques described herein, for example, evaluating, for the same patient, measurements for heart beat intervals (e.g., in a temporal dimension) and use that evaluation to provide a patient or caregiver information an important aspect of the patient's health.

Figure 1:
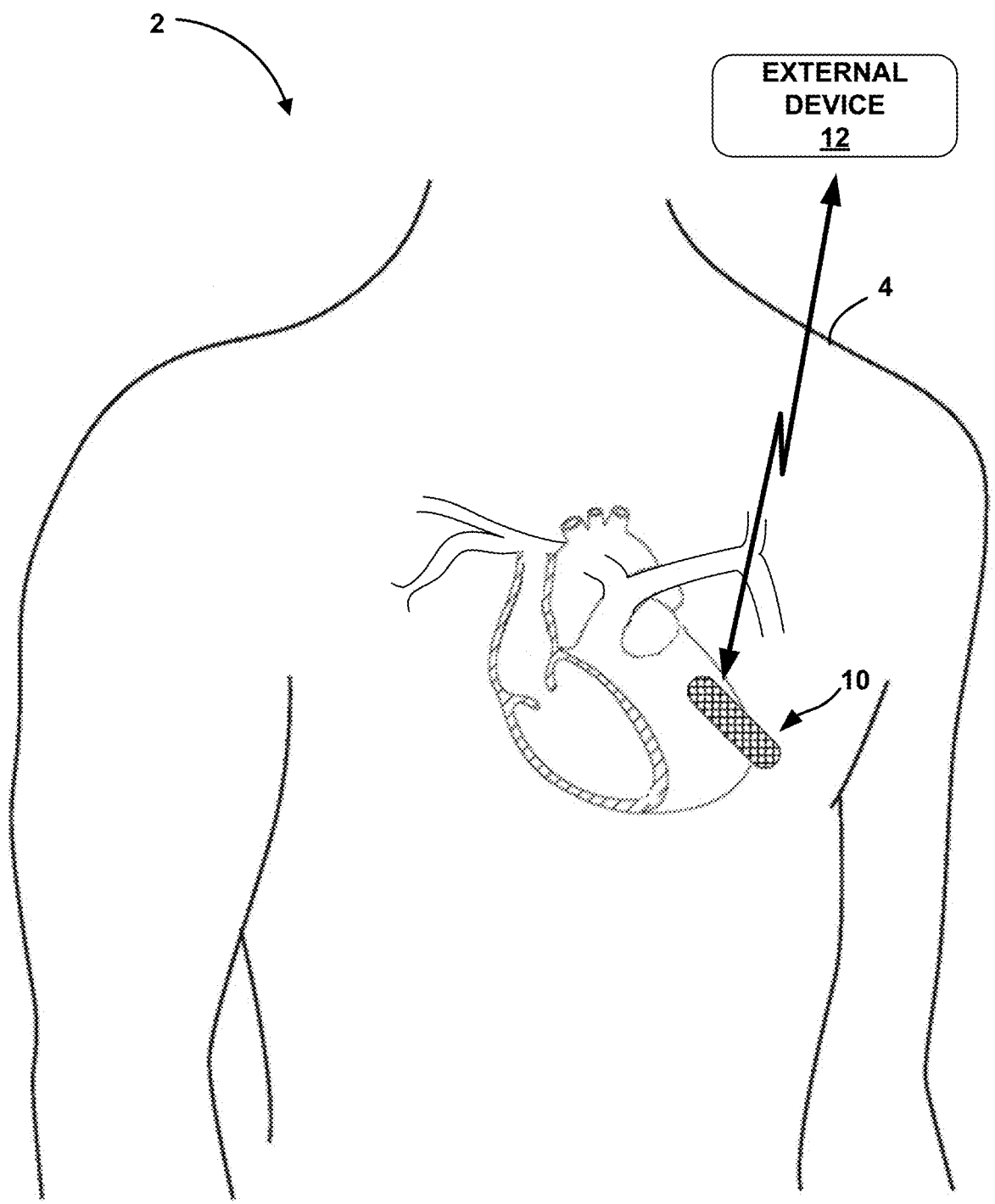
FIG. 1 illustrates example environment of an example medical system in conjunction with a patient, in accordance with one or more examples of the present disclosure.

FIG. 1 illustrates the environment of an example medical system 2 in conjunction with a patient 4, in accordance with one or more techniques of this disclosure. The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 may be positioned on other locations, such as patient 4's cranium region. IMD 10 includes a plurality of electrodes (not shown in FIG. 1), and is configured to sense a cardiac EGM via the plurality of electrodes. In some examples, IMD 10 takes the form of the Reveal LINQ™ ICM. In some examples, IMD 10 includes additional sensors, such as one or more sensors configured to sense patient activity, e.g., one or more accelerometers.

External device 12 may be a computing device with a display viewable by the user and an interface for receiving user input to external device 12. In some examples, external device 12 may be a notebook computer, tablet computer, workstation, one or more servers, cellular phone, personal digital assistant, or another computing device that may run an application that enables the computing device to interact with IMD 10. External device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., radiofrequency (RF) telemetry according to the 802.11 or Bluetooth® specification sets, or other communication technologies operable at ranges greater than near-field communication technologies).

External device 12 may be used to configure operational parameters for IMD 10. External device 12 may be used to retrieve data from IMD 10. The retrieved data may include values of physiological parameters measured by IMD 10, indications of episodes of arrhythmia or other maladies detected by IMD 10, and physiological signals recorded by IMD 10. For example, external device 12 may retrieve cardiac EGM segments recorded by IMD 10 due to IMD 10 determining that an episode of AT or another malady occurred during the segment. As will be discussed in greater detail below with respect to FIG. 5, one or more remote computing devices may interact with IMD 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques for detecting AT episodes of this disclosure. Processing circuitry of IMD 10 may be communicably coupled to one or more sensors, each being configured to sense patient activity, in general, including patient physiological parameters in some form, and sensing circuitry configured to generate sensor data indicative of the sensed patient activity. In some examples, the sensor data sets forth data describing one or more patient physiological parameters associated with cardiac activity. Processing circuitry of IMD 10, possibly in combination with processing circuitry of external device 12, may identify heart beat intervals (e.g., R-waves) in cardiac activity data (e.g., cardiac EGM data) for indicia of non-trivial changes in patient cardiac health due to an occurrence of AT. In some examples, the processing circuitry of medical system 2 analyzes a cardiac EGM sensed by IMD 10 and in response to satisfaction of one or more AT detection criterion, generates (for display) output associated with a detection of an AT episode.

Although described in the context of examples in which IMD 10 that senses patient cardiac activity may comprise an insertable cardiac monitor, example systems including one or more implantable, wearable, or external devices of any type configured to sense the cardiac activity may be configured to implement the techniques of this disclosure.

In some examples, processing circuitry in a wearable device may execute same or similar logic as the logic executed by processing circuitry of IMD 10 and/or other processing circuitry as described herein. In this manner, a wearable device or other device may perform some or all of the techniques described herein in the same manner described herein with respect to IMD 10. In some examples, the wearable device operates with IMD 10 and/or external device 12 as potential providers of computing/storage resources and sensors for monitoring patient activity and other patient parameters. For example, the wearable device may communicate the patient cardiac activity data to external device 12 for storage in non-volatile memory and for applying a first detection criteria or a second detection criteria based on an evidence level of AT in cardiac activity data. Similar to processing circuitry of IMD 10, processing circuitry of external device 12 may analyze the cardiac activity data using either a first detection criteria or a second detection criteria based on an evidence level of AT in cardiac activity data.

Figure 2:
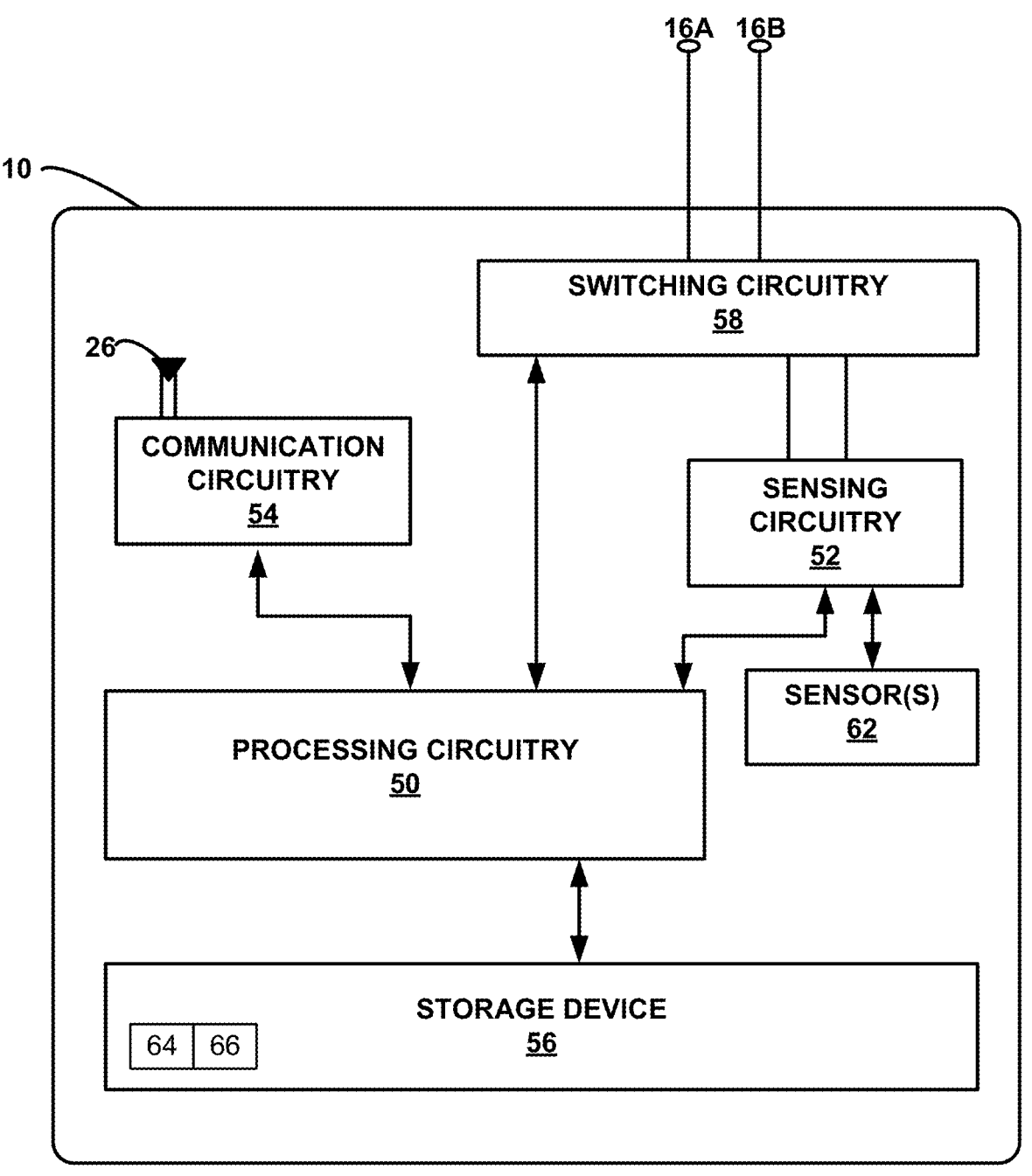
FIG. 2 is a functional block diagram illustrating an example configuration of a medical device, in accordance with one or more examples of the present disclosure.

FIG. 2 is a functional block diagram illustrating an example configuration of IMD 10 of FIG. 1 in accordance with one or more techniques described herein. In the illustrated example, IMD 10 includes electrodes 16A and 16B

(collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to sense electrical signals of the heart of patient 4, for example by selecting the electrodes 16 and polarity, referred to as the sensing vector, used to sense a cardiac EGM, as controlled by processing circuitry 50. Sensing circuitry 52 may sense signals from electrodes 16, e.g., to produce a cardiac EGM or ECG, in order to facilitate monitoring the electrical activity of the heart. In some examples, sensing circuitry 52 may include one or more filters and amplifiers for filtering and amplifying signals received from electrodes 16 and/or sensors 62.

Sensing circuitry 52 may monitor sensors 62, which may include one or more accelerometers, pressure sensors, and/or optical sensors, as examples. Sensing circuitry 52 may capture signals from any one of sensors 62, e.g., to produce patient data including cardiac activity data 64, in order to facilitate monitoring the patient activity and detecting changes in patient health. Sensing circuitry 52 may generate sensor data corresponding to patient cardiac activity (e.g., cardiac mechanical activity) from the sensor signals received from sensor(s) 62 that encode the patient cardiac activity. Sensing circuitry 52 and processing circuitry 50 may store cardiac activity data 64 in storage device 56 as an arrangement of the sensor data, e.g., of intervals between cardiac depolarizations/contractions or digitized samples of the sensor signals, for use by detection logic 66.

Processing circuitry 50, executing detection logic 66 configured to perform a detection analysis on the cardiac activity data 64, is operative to detect a change (e.g., a decline) in patient health due to an occurrence of an AT. Processing circuitry 50 may control sensing circuitry 52 and/or electrodes 16 to sense cardiac activity in some form as described herein and then, determine whether that cardiac activity indicates an episode of an AT. In this example, processing circuitry 50 is configured to first, determine an evidence level for the AT episode, second, determine which detection criteria to apply based on the evidence level, and third, apply an appropriate set of detection criteria to the cardiac activity data.

IMD 10 is a medical device that implements detection 66 with an innovative dichotomy of different detection criteria whose application is dictated based upon an evidence level (LATE). A number of medical devices described herein monitor patient 4's cardiac activity with an AT detection feature and because of the innovative dichotomy, that detection feature is viable. Previously, due to a relatively low detection performance, a similar feature was infrequently used by physicians. The detection criteria described herein improves upon low detection performance and enables this feature for LINQ and other ICMs. In this manner, the techniques of this disclosure may advantageously enable improved accuracy in the detection of changes in patient health and, consequently, better evaluation of the condition of the patient.

Processing circuitry 50 of IMD 10 tracks heart beats over time to measure regularity and/or irregularity of heart beat intervals. There are a number of mechanisms (e.g., metrics) for converting the cardiac activity data into one or more regularity measures and/or one or more irregularity measures, which may be a quality (e.g., high activity, low activity, and/or the like) or a quantity (e.g., a number of minutes or fractional minutes), and then, computing the evidence level from the one or more regularity measures and/or one or more irregularity measures.

Processing circuitry 50 of IMD 10 may execute detection logic 66 programmed with multiple sets of detection criteria; based on the evidence level of AT in cardiac activity data, processing circuitry 50 of IMD 10 applies a set of detection criteria set most likely to produce an accurate assessment of the cardiac activity data for indicia of AT. In one example, processing circuitry 50 records two or more minutes of heart beat intervals, computes a regularity term and an irregularity term for the record heart beat intervals, and then, computes the evidence level to determine which detection criteria is worth analyzing for any indication of AT.

Processing circuitry 50 of IMD 10 determines which detection criteria to apply based on the evidence level. The evidence level may include a numerical value; if that value exceeds a threshold value, processing circuitry 50 of IMD 10 identifies the evidence level as being indicative of relatively regular heart beat intervals, but if not, processing circuitry 50 of IMD 10 identifies the evidence level as being indicative of relatively irregular heart beat intervals. By "relatively regular" or "relatively irregular", the present disclosure refers to a mathematical measure that, according to a well-defined scale, describes consistency (or regularity) of individual or multiple waveforms (e.g., R-waves) in cardiac EGM signals.

Processing circuitry 50 of IMD 10 may use the evidence level to select the appropriate set of detection criteria to apply to the cardiac activity data. In some examples, if the evidence level indicates relatively regular heart beat intervals (e.g., R-waves), processing circuitry 50 of IMD 10 applies a first set of AT detection criteria; otherwise, if the evidence level indicates relatively irregular heart beat intervals (e.g., R-waves), processing circuitry 50 of IMD 10 applies a second set of AT detection criteria.

One example equation for the evidence level is $\mathcal{L}_{ATE}=\mathcal{L}_{IE}+\mathcal{L}_{AE}+\mathcal{L}_{DE}\ \mathcal{L}_{RE}-4\ \mathcal{L}_{PE}$. In this equation, irregularity measure ($\mathcal{L}_{IE}$) and regularity measure ($\mathcal{L}_{RE}$) of the RR intervals of a suspected AT episode is fundamental to determining the evidence level. RR interval refers to the time elapsed between two successive R-waves of the cardiac EGM signal (e.g., patient cardiac activity stored as cardiac activity data 64). In addition, the evidence level is based on Density evidence ($\mathcal{L}_{DE}$) measures the density of the distribution of ($\delta RR(i)$, $\delta RR(i-1)$) in a cluster. Anisotropy evidence ($\mathcal{L}_{AE}$) measures the orientation of the distribution. Premature atrial contraction evidence ($\mathcal{L}_{PE}$) measures the presence of a dense distribution in segments (e.g., inter-quartile ranges) which is a characteristic of compensatory pauses.

Figure 7:
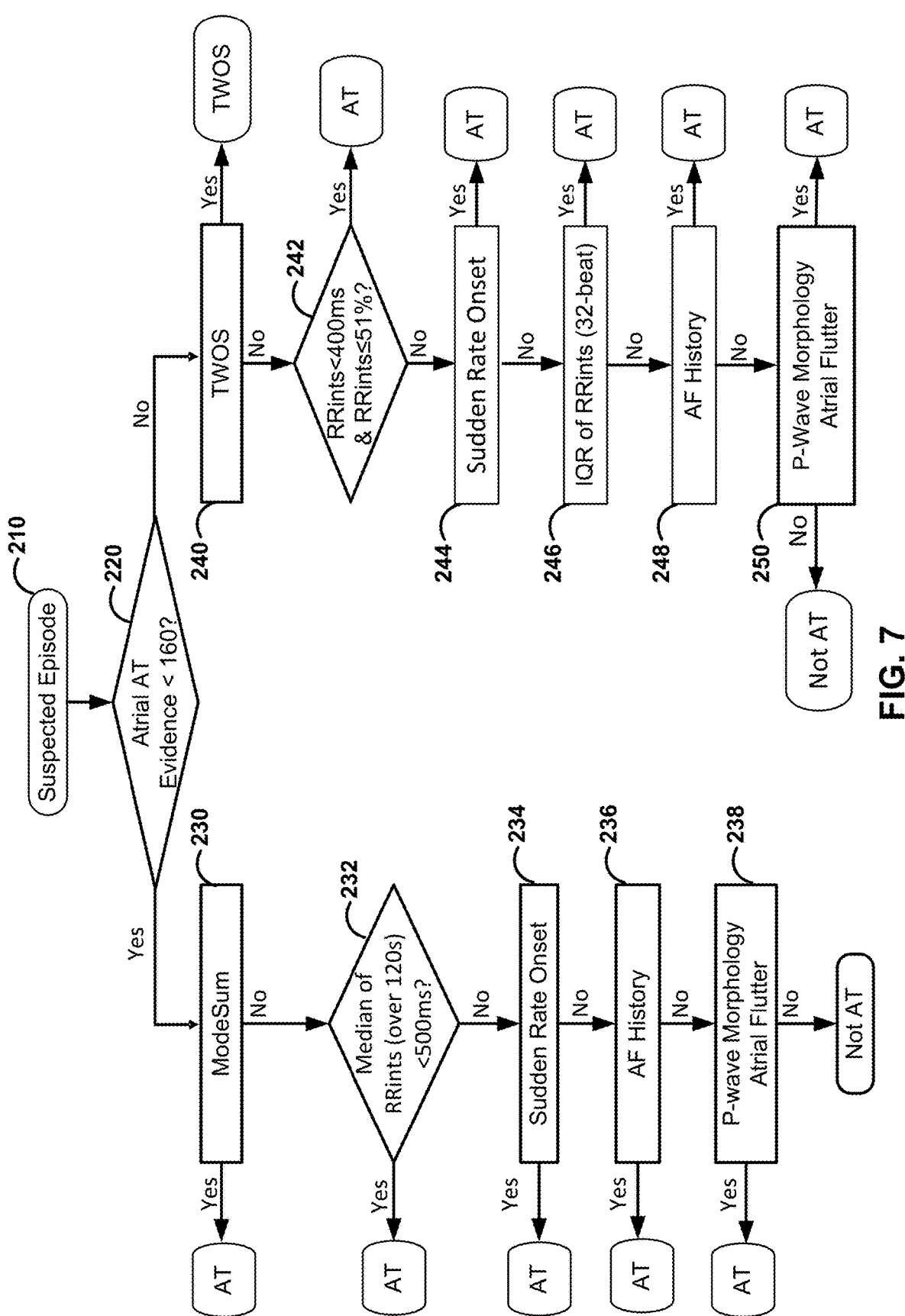
FIG. 7 is a flow diagram illustrating an example decision tree to enable detection of an AT episode, in accordance with one or more examples of the present disclosure.

Once processing circuitry 50 of IMD 10 determines the evidence level, processing circuitry 50 of IMD 10 applies one of two innovative sets of detection criteria. Both sets can be assembled into a decision tree, which is illustrated in FIG. 7, where each branch represents a portion of detection logic 66 for evaluating one of these criteria sets. For example, if cardiac activity data 64 of an episode (e.g., a segment suspected to be cardiac episode) has an AT evidence level less than 160 (i.e., a regular episode), the medical device proceeds to evaluate the episode data using a first branch's set of criteria. Processing circuitry 50 of IMD 10 evaluates ModeSum sub-criteria using the episode data. If the episode data passes the ModeSum check, it is detected as a true AT episode. The ModeSum criteria may determine, for example, when x % (e.g., x=97, 95, 90, 85, or 80) of RR intervals are within three bins (e.g., where each bin's width is 10 ms) and/or more than n % (e.g., n=70, 65, 60, 51) of all RR intervals are in one bin (i.e., Mode bin), that episode data is determined to be a true AT episode because of being highly regular in nature. If, on the other hand, the episode data fails to pass the ModeSum criteria, the medical device proceeds to determine whether the episode data has a median of RR intervals (over 120 s) less than a programmable threshold (e.g., 500 ms). If the episode data has a median of RR intervals (over 120 s) value less than the programmable threshold (e.g., 500 ms), then the episode data is considered to be indicative of a true AT episode. If not, the episode data is then passed for evaluation with Sudden Rate Onset criteria. When the episode data passes Sudden Rate Onset criteria, it is considered an AT. If the episode data does not satisfy the sudden rate onset criteria, processing circuitry 50 of IMD 10 classifies the episode data as indicative of a Non-AT episode.

For an episode with AT evidence level equal to or higher than 160, episode data is passed to the other branch of the decision tree. In some examples, T-wave oversensing (TWOS) rejection and High Heart Rate feature are applied to suspected episodes with AT Evidence greater than or equal to 160. Processing circuitry 50 of IMD 10 determines whether the episode satisfies the TWOS sub-criteria and if so, the episode is considered as a TWOS episode and rejected immediately. Otherwise, processing circuitry 50 of IMD 10 applies High Heart Rate sub-criteria (e.g., whether more than X % of RR intervals are less than 400 ms where X is a percentage value can vary from 51% to 60% or 65%). If an episode is not rejected for TWOS, High Heart Rate feature can accurately classify that episode as a true AT episode if a heart rate is determined to be 150 bpm or higher (i.e., which happens when RR intervals are less than 400 ms). If the episode passes high heart rate criteria, processing circuitry 50 of IMD 10 classifies that episode data as an AT episode; if not, the episode is evaluated using Sudden Rate Onset criteria. Similar to the other branch of the tree, if the episode data satisfies the Sudden Rate Onset criteria, it is considered as AT; if not, then it is sent for Interquartile range check of RR intervals for every 32-beat. If the episode passes the IQR check it is considered as AT, and if not then it is rejected as Non-AT episode.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth, WiFi, or other proprietary or non-proprietary wireless communication schemes.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include various patient data as described herein (e.g., patient physiological parameters such that those described herein corresponding to cardiac activity) and episode data for detected ATs.

Figure 3:
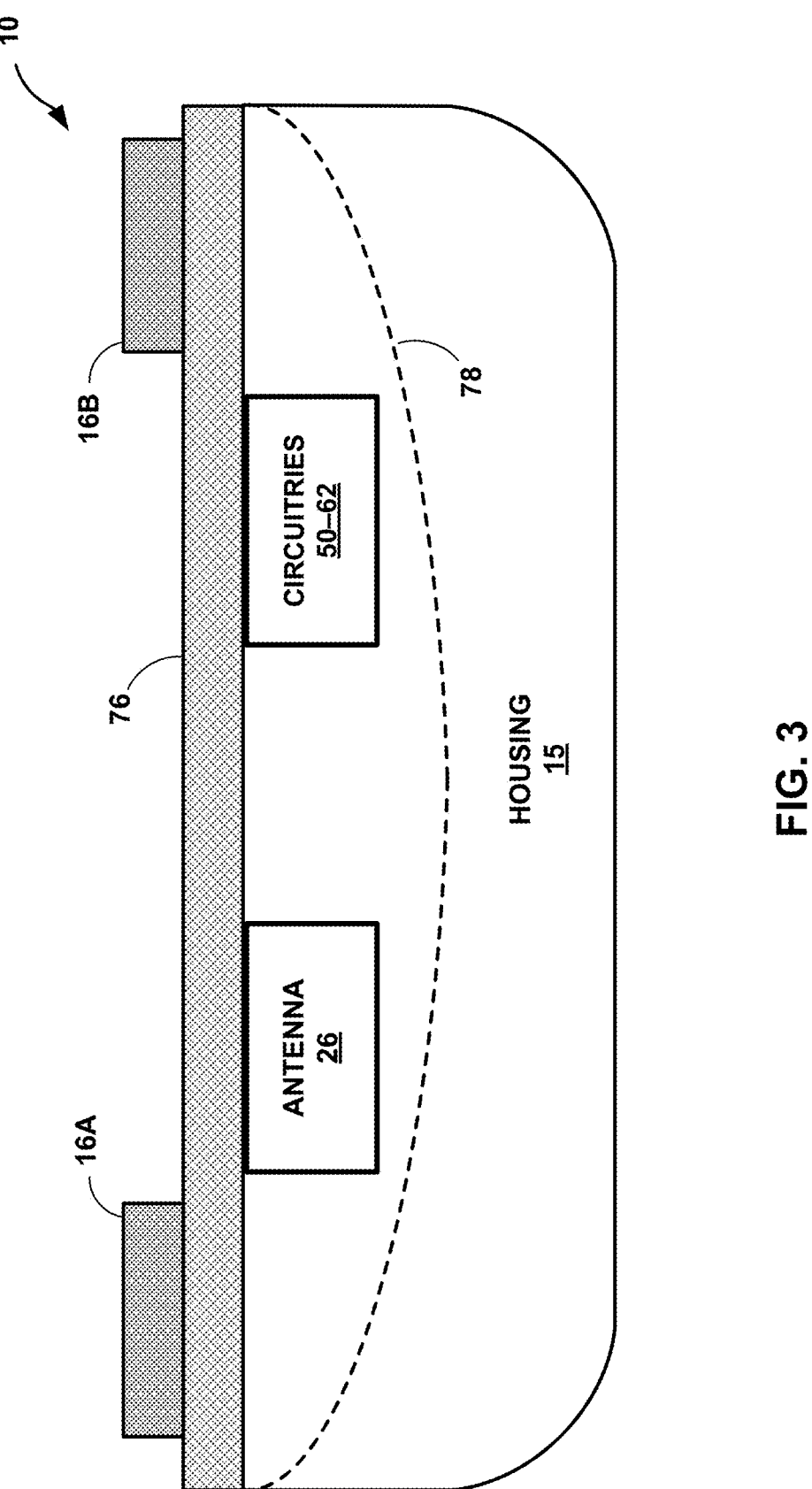
FIG. 3 is a conceptual side-view diagram illustrating an example configuration of the IMD of FIGS. 1 and 2, in accordance with one or more examples of the present disclosure.

FIG. 3 is a conceptual side-view diagram illustrating an example configuration of IMD 10 of FIGS. 1 and 2. While different examples of IMD 10 may include leads, in the example shown in FIG. 3, IMD 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
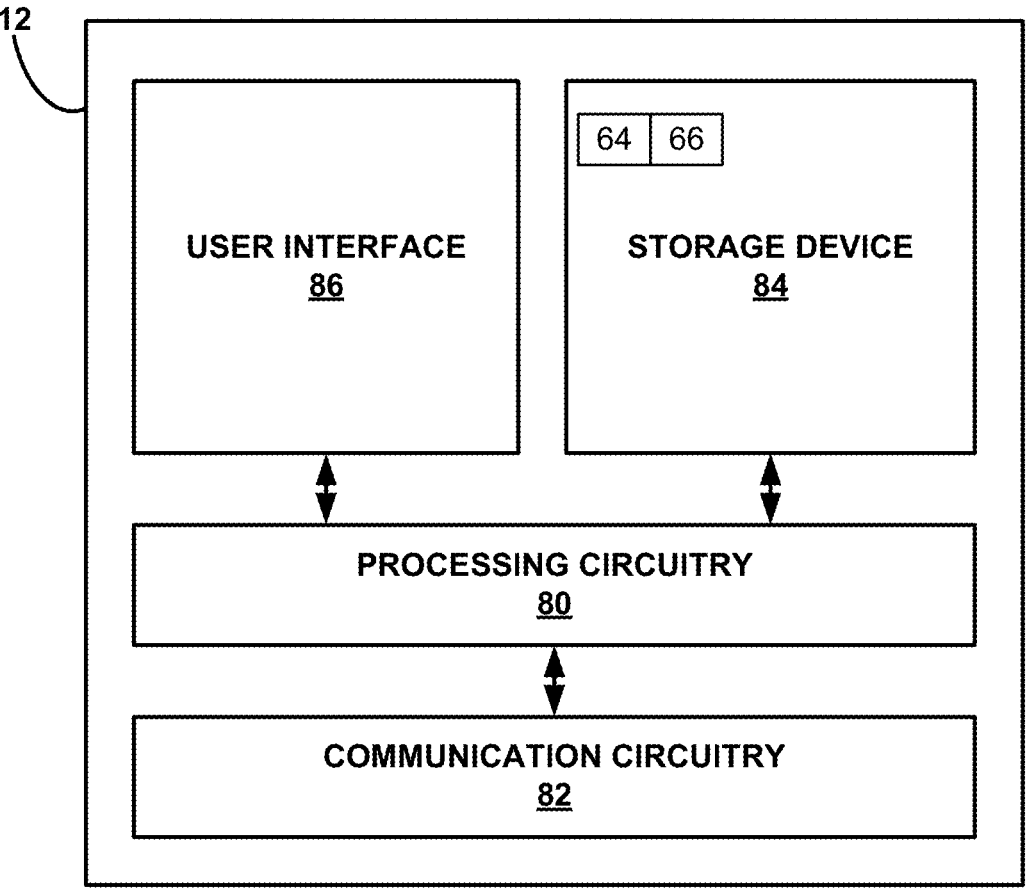
FIG. 4 is a functional block diagram illustrating an example configuration of the external device of FIG. 1, in accordance with one or more examples of the present disclosure.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, NFC, RF communication, Bluetooth, WiFi, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., asystole episode data) to external device 12. In turn, external device 12 may receive the collected data from IMD 10 and store the collected data in storage device 84. The data external device 12 receives from IMD 10 may include patient data such as cardiac activity 64, which as described herein refers to patient 4's cardiac activity (e.g., cardiac EGMs) in a form of one or more physiological parameters. In general, cardiac activity data for any patient is based on sensor data generated by IMD 10 and/or external device 12, and further based on episode data identifying portions of the cardiac activity indicative of detected or suspected ATs. Processing circuitry 80 may implement any of the techniques described herein to analyze patient data (e.g., cardiac activity data 64) from IMD 10 to determine an evidence level of an AT episode based on heart beat intervals in the cardiac activity data e.g., to determine whether the patient is experiencing a change in health e.g., based upon one or more criteria.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., evidence levels of heart beat intervals, indications of a detection of an AT, indications of changes in patient health that correlate to the AT detections, and visualizations of various sensor data such as cardiac EGM or ECG data. In addition, user interface 86 may include an input mechanism configured to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Similar to IMD 10, processing circuitry 80 of external device 12 may be configured with detection logic 66 that, when executed and run as a computing application, is operative to analyze cardiac activity data 64 of patient 4 for evidence of cardiac issues likely to cause a decline in patient 4's overall health. Some issues constitute cardiac events, such as an AT episode, and detection logic 66 evaluates the above cardiac activity data for indicia of such events. With respect to detecting occurrences of AT in particular, a mechanism (e.g., machine learning model including a decision tree) is programmed into detection logic 66 and that mechanism as described herein only applies detection criterion that is likely to produce an accurate classification.

Processing circuitry 80 of external device 12 executes detection logic 66 (and/or processing circuitry 50 of IMD 10) to determine an evidence level of an AT episode based on heart beat intervals in cardiac activity data 64 over a pre-determined time period. The evidence level may be computed from at least one regularity measure and at least one irregularity measure of the heart beat intervals (e.g., R-waves). In some examples, multiple sets of detection criteria are programmed into detection logic 66 where each set is appropriate for a particular class (e.g., portion) of the cardiac activity data and leverages an AT episode evidence level as a determinative factor in selecting the set that is most suitable for any given a cardiac EGM segment.

Processing circuitry 80, based on a determination that the evidence level indicates relatively regular heart beat intervals over the pre-determined time period, is configured to apply a first set of AT detection criteria to the cardiac activity data and then, indicate a detection of an AT episode based on based on satisfaction of at least one of the first set of AT detection criteria. Processing circuitry 80 may generate for display output indicating a detection of an AT episode based on a determination that the satisfaction of the first set of AT detection criteria indicates substantially regular heart beat intervals over the pre-determined time period. By "substantially regular heart beat intervals", the present disclosure describes heart beat (e.g., ventricular) intervals that are at a higher level of regularity than regular heart beat intervals.

Processing circuitry 80, based on a determination that the evidence level indicates relatively irregular heart beat intervals over the pre-determined time period, is configured to apply a second set of AT detection criteria to the cardiac activity data and then, indicate a detection of an AT episode based on satisfaction of at least one of the second set of AT detection criteria. The second set of AT detection criteria may include at least one criterion different from the first set of AT detection criteria. Processing circuitry 80 may generate for display output indicating a detection of a non-AT episode based on a determination that the satisfaction of the second set of AT detection criteria indicates T-wave over-sensing. In other examples, processing circuitry 80 generates for display output indicating a detection of an AT episode based on a determination that the satisfaction of the second set of AT detection criteria indicates a sudden change in ventricular rate.

Figure 5:
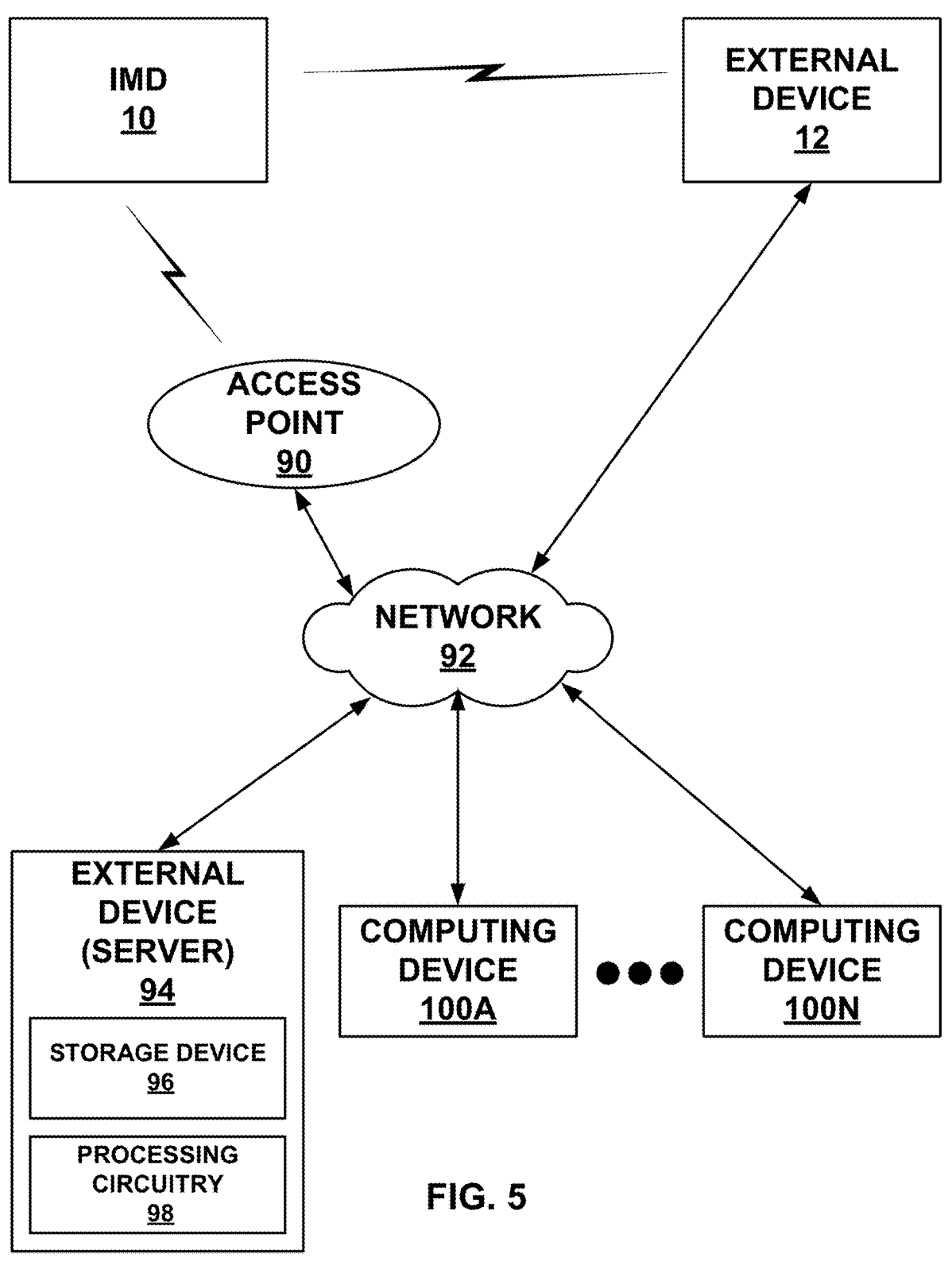
FIG. 5 is a block diagram illustrating an example system that includes an access point, a network, external computing devices, such as a server, and one or more other computing devices, which may be coupled to the medical device and external device of FIGS. 1-4, in accordance with one or more examples of the present disclosure.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as patient cardiac activity data and indications of episode data, and/or indications of changes in patient health, to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, one or more of computing devices 100 may be a tablet or other smart device located with a clinician, by which the clinician may program, receive alerts from, and/or interrogate IMD 10. For example, the clinician may access patient data and/or indications of patient health collected by IMD 10 through a computing device 100, such as when patient 4 is in between clinician visits, to check on a status of a medical condition. In some examples, the clinician may enter instructions for a medical intervention for patient 4 into an application executed by computing device 100, such as based on a status of a patient condition determined by IMD 10, external device 12, server 94, or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze information or data received from IMD 10, e.g., to determine whether the health status of a patient has changed.

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
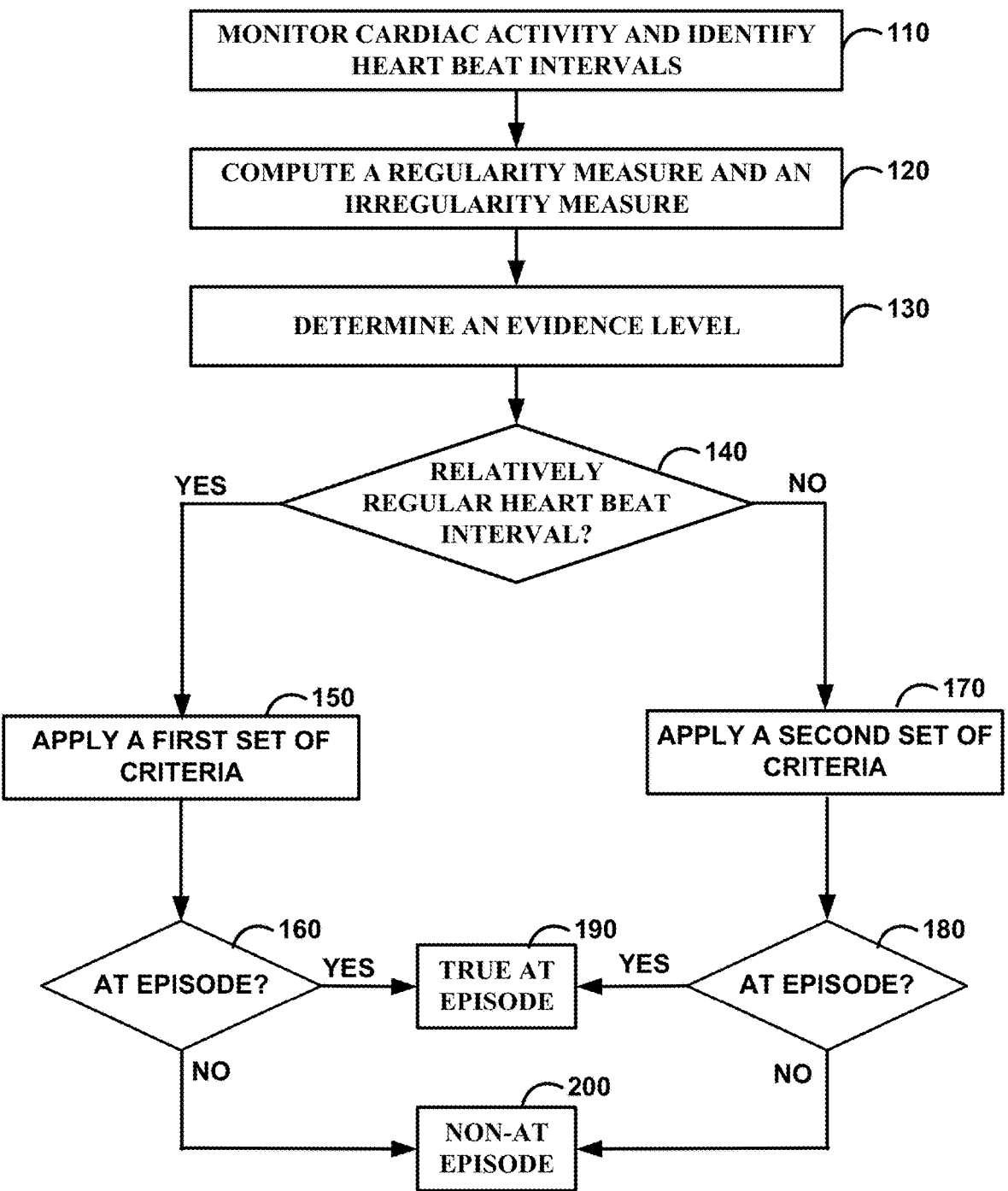
FIG. 6 is a flow diagram illustrating an example operation for detecting an atrial tachycardia (AT) episode, in accordance with one or more examples of the present disclosure.

FIG. 6 is a flow diagram illustrating an example operation for detecting an AT episode, in accordance with one or more examples of the present disclosure. In some examples, the example operation may be implemented, by a medical device (e.g., an implantable or insertable medical device) or an external device, for determining whether to render a prediction/detection based on certain criteria.

One or more processors of a medical device, such processing circuitry 50 of IMD 10, monitors patient 4's cardiac activity over a period of time, including the generation of patient cardiac activity data by sensing circuitry 52 of IMD 10, and identifies individual heart beats and determines heart beat intervals (110). Heart beat intervals—which, as an alternative, may be referred to as ventricular intervals—generally span R-waves.

According to the illustrated example of FIGS. 1-5, processing circuitry 50 of IMD 10, processing circuitry 80 of external device 12, processing circuitry 98 of external device 94, and/or one or more other processors may perform techniques described herein. The example operation of FIG. 6 is described herein using elements of FIGS. 1-2, for the sake of brevity, and processing circuitry 50 of IMD 10 is used herein to represent any combination of the above processing circuitry embodiments.

Processing circuitry 50 of IMD 10 computes a regularity measure and an irregularity measure (120) and based on both measures, determines an evidence level (130). For example, as discussed in greater detail with respect to FIGS. 1-2, processing circuitry 50 may monitor the patient cardiac activity data, including cardiac EGMs, over a pre-determined time period of a number of hours and/or days and initiates, continuously, periodically, and/or under certain circumstances, logic circuitry (e.g., detection logic 66) to detect an instance of an AT episode in the cardiac EGMs. Processing circuitry 50 of IMD 10 may determine an AT episode evidence level based on heart beat intervals (e.g., a cardiac depolarization such as a R-wave) within the cardiac EGM in the cardiac activity data.

The evidence level guides the detection analysis as described herein. Some medical device achieve a reduction in the number of criteria used in the detection analysis such that the processing circuitry applies a set of detection criteria most likely to detect a true atrial tachycardia (AT), in some instances, without exceeding a minimum number (e.g., zero or more) of false determinations. These criterion may correlate with a highest likelihood for a true AT, for example, in terms of specificity, sensitivity, and so forth.

Processing circuitry 50 of IMD 10 proceeds to determine whether the evidence level indicates relatively regular heart beat intervals (140) and renders a determination that prompts application of either a first set of detection criteria or a second set of detection criteria. Based on a determination that the evidence level indicates relatively regular heart beat intervals (YES branch of 140), processing circuitry 50 of IMD 10 applies the first set of criteria (150). Based on that application, processing circuitry 50 of IMD 10 determines whether the first set of criteria is satisfied (e.g., whether one, more than one, or all of the first criteria are satisfied) and if so, processing circuitry 50 of IMD 10 determines whether the satisfaction indicates an AT episode (160).

On other hand, based on a determination that the evidence level indicates relatively irregular heart beat intervals (NO branch of 140), processing circuitry 50 of IMD 10 applies a second set of criteria that is different from the first set of criteria (170). In some examples, heart beat interval regularity or irregularity may be referred to as ventricular interval regularity or irregularity. Based on the application of the second set of criteria, processing circuitry 50 of IMD 10 determines whether the second set of criteria is satisfied (e.g., whether one, more than one, or all of the second criteria are satisfied) and if so, processing circuitry 50 of IMD 10 determines whether the satisfaction indicates an AT episode (180).

Based on the satisfaction of either the first set of criteria or the second set of criteria, processing circuitry 50 of IMD 10 proceeds to generate, for display, output indicative of a true AT episode (190). On the other hand, if neither the first set of criteria nor the second set of criteria are satisfied, processing circuitry 50 of IMD 10 proceeds to generate, for display, output indicative of a non-AT episode or a non-episode (200).

In the example operation of FIG. 6, it is noted that there is a range of pre-determined options that may be programmed into examples of processing circuitry 50 of IMD 10. There are a number of available configurable parameters to direct performance of the example operation of FIG. 6. Some parameters as described herein specify which features to implement into the above first and/or second sets of criteria and, possibly, one or more parameters to influence an ordering of the features in a flow of the detection logic 66. One example model (e.g., a decision tree) that results from implementing an example set of parameters, as illustrated in FIG. 7, prescribes a flow in which the first and second sets of detection criteria are applied to cardiac activity data having relatively regular heart beat intervals and relatively irregular heart beat intervals, respectively; based on time values of the relatively irregular heart beat intervals, the example model directs application of a ModeSum feature followed by a first statistical evaluation (e.g., of the heart rate) and then, a Sudden Rate Onset feature and based on time values of relatively regular heart beat intervals, the example model directs application of TWOS Rejection feature followed by a second statistical evaluation (e.g., of the heart rate), a same or similar Sudden Rate Onset feature, and then, a Sudden Regularity/Irregularity feature. Each statistical evaluation may include a threshold value comparison of the patient's heart rate as computed from the cardiac activity data. The present disclosure may refer to the first and the second statistical evaluation as Heart Rate features; for example, the second statistical evaluation may be referred to as High Heart Rate feature. Each feature includes sub-criteria and, except for TWOS rejection criteria, satisfaction of each criterion is indicative of the cardiac activity data being a true AT episode. For each feature's sub-criteria, a number of additional parameters, settings, options, etc. are configured to modify application of that sub-criteria, causing dynamic and/or static changes in the performance.

Some configurable parameters, when implemented into detection logic 66, cause processing circuitry 50 of IMD 10 to program one or more optional features into the example model such that one or more additional criterion may be appended to either the first or second sets of detection criteria. The example model may extend the first and/or second set of criteria programmed into detection logic 66 with additional criterion such that, under certain circumstances, processing circuitry 50 of IMD 10 applies the criterion; however, in other circumstances, processing circuitry 50 of IMD 10 determines to skip or omit the additional criterion. Designating a feature as optional is another configurable parameter.

As further illustrated in FIG. 7, an optional feature (which may be referred to herein as "No. of RRints in static range" feature) includes an additional criterion for the second set of detection criteria. If the cardiac activity data is determined to include relatively irregular heart beat intervals and other features of the second set of detection criteria fail to detect a true AT episode, applying the additional criterion most likely produces an accurate determination as whether the cardiac activity data is an AT.

To illustrate by way of an example suspected episode that does not pass the Sudden Regularity/Irregularity feature (e.g., Interquartile Range (IQR) check of RR intervals (32-beat) criterion), time values for that episode are evaluated to determine satisfaction of the additional criterion. One purpose for the additional criteria is to measure a change from regularity to irregularity or, vice versa, from irregularity to regularity (e.g., time range). If the episode's time values meet or exceed a minimum number of RR intervals in a static range, there is a substantial change from regularity to irregularity (e.g., irregularity onset) and, most likely, the episode is a true AT. In one example, the minimum number of RR intervals in a static range may be set to a static threshold or may be a configurable parameter that the user defines prior to executing detection logic 66 and evaluating the example suspected episode. Instead of a pre-determined value, the minimum number may represent a dynamic threshold that is established during the execution of detection logic 66 and based on various factors. In another example, the additional criterion may set the static range to range of time defined as a median time value with a time buffer in both temporal directions (i.e., +/−50 ms). Satisfaction of both example thresholds passes the feature's sub-criteria and the cardiac activity data may be considered as AT; if not, the cardiac activity data is considered as a Non-AT episode. Given a limited subset of time values and other cardiac activity data for relatively irregular heart beat intervals and the prior knowledge (e.g., observations) that each preceding feature failed, there is a high probability or likelihood that detections of AT are accurate. In this manner, the example model avails the "No. of RRints in static range" feature's high accuracy level achieved by focusing the additional criterion on the limited subset. Implementing this optional feature reduces false detections of non-AT episodes that are in fact true AT episodes and by increasing a probability of an accurate determination, the optional feature increases sensitivity.

Some configurable parameters are operating mode settings configured to fine-tune performance of detection logic 66 (i.e., the above example model) including a higher sensitivity mode, a higher specificity mode, and/or the like. Higher sensitivity mode directs application of the ModeSum feature to be less strict, e.g., changing the 3-bin-count threshold to 85% from default 90% of all RR intervals or loosen the parameters used for sudden rate onset detection as well as changing some other parameters of the decision tree to make it more sensitive. Higher specificity mode directs applicating of the ModeSum feature using stricter parameters than default parameters for AT episodes detection, e.g., changing ModeSum 3-bin-count threshold to 95% from default 90% of all RR intervals or changing sudden rate onset detection parameters to higher values, e.g., changing difference value corresponding to comparison between 12-beat block median before and 12-beat block median after a specific heart beat to greater than 20% instead of the default 15% as well as changing other parameters of the decision tree to make it more specific.

There are additional features, which may or may not be optional during execution of detection logic 66, to improve current True AT detection sensitivity as well as provide detection logic 66 the flexibility to switch to one of two different modes (e.g., higher sensitivity mode and higher specificity mode) when necessary. The following describes non-limiting examples where one or more additional features may be incorporated into detection logic 66. It is possible for the following additional features to be the only features in detection logic 66 (e.g., decision tree model of FIG. 7) according to other examples or, as an alternative, be applied separately from one or more features described herein (e.g., for decision tree model of FIG. 7).

IMD 10 may maintain a history of past cardiac episodes for patient 4. One example feature, patient Atrial Fibrillation (AF) History feature, leverages a medical device's Atrial Fibrillation (AF) episode detection capabilities and accuracy level to improve that device's AT episode detection capabilities. Detection logic 66 in IMD 10 may detect AF episodes based on incoherence of RR intervals as well as evidence of single p-waves between two R-waves. An example dataset for this history may include data attributes (e.g., in a tuple) of which at least one data attribute describes a particular determination, by IMD 10 or another medical device, regarding whether patient cardiac activity correlates with a cardiac episode of some type. While IMD 10 may record cardiac episodes regardless of type or, as an alternative, cardiac episodes of a specific type or types (e.g., both AF and AT episodes), an example AF history delineates instances where IMD 10 detected an occurrence of an AF cardiac episode. The example AF history may correspond to a configurable time period (e.g., 1 or 2 days) given that the recency of a detected AF episode factors into the relationship with AT detection. As an option, the example AF history may indicate a final determination as to whether the suspected AF cardiac episode was later rejected as a false positive or confirmed as a true positive. A number of alternative approaches are possible; for instance, the example AF history may identify one or more false negatives or true negatives in patient 4's cardiac activity. In this alternative approach, "episode data" may refer to patient 4's recorded cardiac activity data over a fixed time period and not necessarily to a suspected cardiac episode. A number of additional data attributes have been described in the present disclosure.

Detection logic 66 may implement an example AF history feature (e.g., in the decision tree) to detect true AT episodes from the cardiac activity data of patient 4. In general, the AF history is generated to be descriptive of patient 4's cardiac health and that data provides intelligence into patient 4's likelihood or probability of having a true AT episode. In addition to AF history data, IMD 10 may store information indicative of patient 4's normal/abnormal cardiac activity, specifically when patient 4's is experiencing or about to experience a true cardiac episode (e.g., a true AF episode). Upon detecting each AF episode, detection logic 66 may increment the AF count and/or compute, as an (e.g., aggregated) value, a number of detected AF episodes.

An example AF history feature, as described herein, may define one or more criterion that, when applied to various attributes of the AF history, provides insight into patient 4's cardiac physiology. In some examples, the AF history feature sub-criteria may be dispositive of the suspected episode while in other examples, additional features are invoked to improve upon an accuracy of any detected AT episode under this feature. Detection logic 66 may incorporate, into a decision tree model, the AF history feature in combination with other features described herein or the AF history feature may be invoked without additional feature sub-criteria.

One example AF history criterion may be directed to determining that cardiac activity data 64 is indicative of a true AT episode based on a comparison between the AF history data described herein and a threshold or thresholds. Detection logic 66 of IMD 10 may store a record in AF history data for each AF episode lasting at least a certain duration (e.g., one hour) in length. According to one example AF history criterion, having at least one such AF episode in a recent past (e.g., a configurable number of days) implies that the suspected episode of cardiac activity data 64 most likely is a true AT episode. For instance, detection logic 66 of IMD 10 may store, in the AF history data of patient 4, a daily count of detection AF episodes and in response to a cardiac EGM suspected of being an AT episode, may confirm that the cardiac EGM is a true AT episode and generate output data indicative of that positive detection if, for each day of the past week, the AF daily count is non-zero. In contrast, having a lack of detected AF episodes in the recent past of patient 4 indicates that the suspected AT episode most likely is a non-AT episode or even a non-episode. In some examples, detection logic 66 may continue evaluating the suspected AT episode and cardiac activity data 64 with other features, for instance, if the AF history feature cannot be used to accurately identify the suspected episode as a true AT episode, a non-AT episode, or a non-episode. In other examples, if the example AF history criterion is not satisfied, detection logic 66 may generate output data indicative of the rejection of the AT episode and/or apply another mechanism (e.g., another model) to classify the suspected AT episode as a different type of episode.

IMD 10's detection rate for AT benefits from IMD 10's high detection rate for AF episodes (e.g., a sensitivity more than 99% and specificity more than 99%) given a physiological relationship between AF and AT. One goal underpinning criterion of an AF history feature is to use historical episode data to program detection logic 66 to be more sensitive for AT detection. If there is a history of AF episodes for patient 4, detection logic 66 may invoke at least one AF history feature criterion to determine whether that history renders patient 4 (e.g., and their cardiac activity data) more likely or less likely to have a true AT episode. In the AF history (or general episode history) of patient 4, detection logic 66 has access to various data attributes including AF burden trend, AF count, a reason for monitoring such as a Boolean value indicating whether patient 4 received their medical device for management/monitoring of AF episodes or other cardiac episodes)) and may be configured to use any combination of these attributes to increase overall sensitivity of detection logic 66.

Another example feature, Distinct Heart Rate feature, leverages information regarding a particular type of Atrial Flutter a patient has to determine whether the patient has True AT or not. The feature will look for specific ratios in heart rate changes. For example, if a patient has 1:1 AT with a ventricular rate/heart rate of 150 bpm (i.e., RR intervals of 400 ms), and then it changes to 2:1 AT, heart rate should change to 75 bpm (i.e., RR intervals of 800 ms) or if it jumps from 3:1 AT with a ventricular rate of 100 bpm (i.e., RR intervals of 600 ms) to 4:1 AT, the ventricular rate should change to around 75 bpm (i.e., RR intervals of 800 ms). That means, in the case of AT or Atrial Flutter, changes in heart rate (or RR interval) are not random or continuous; instead, they follow particular patterns or ratios. This distinct ratio of heart rate change may be referred to as an example of "Distinct Heart Rate" feature. Incorporating this feature in detection logic 66 (e.g., the decision tree model of FIG. 7) increases sensitivity significantly.

Yet another example, Increased Sensitivity for recent Sudden Onset detections feature, combines criterion from both sudden rate onset and sudden regularity/irregularity onset features and advantageously uses information learned from one feature in another feature's determination. If a sudden onset (rate or regularity/irregularity) based True AT episode is detected recently in a patient, then the algorithm will switch to higher sensitivity mode for that particular patient since there is a comparatively high chance that the detected episodes are True AT episodes. This feature may improve detection logic 66's sensitivity significantly.

Another example feature, Increased Specificity for Short AT detections feature, directs detection logic 66 to apply a criterion under a default mode unless a proclivity of short AT detections indicate a false AT episode, in which case, detection logic 66 is to apply a criterion under a different operating mode, such as a higher specificity mode. Unlike other features, this feature is designed to increase specificity more than sensitivity. For instance, when patients have a pattern of frequent AT detections of short episode length, these are typically false detections. In such cases, detection logic 66 may decide to switch to higher specificity mode for those particular patients, since most likely the newly detected episodes are false AT episodes. For other patients, detection logic 66 may remain in default mode, i.e., higher sensitivity and lower specificity.

In one example, processing circuitry 50 of IMD 10 determines whether IMD 10 is programmed to extend and/or change detection logic 66 (e.g., while running in IMD 10). This may include any of the above and/or any of the following additional features. It should be noted that the present disclosure envisions other features to possibly employ in a medical device. Some additional features may be used independently from any other AT evidence (e.g., in a separate set of detection criteria). One example feature may be referred to as P-wave morphology feature. P-wave Morphology feature was used to differentiate Atrial Flutter waves from regular P-waves. In some examples, this feature and/or other additional features are appended at the end of both branches of a decision tree model, significantly improved the overall True AT detection performance.

The P-wave morphology feature described herein may be configured to identify an Atrial Flutter (AFL) episode in patient 4 from cardiac activity data 64 and (possibly) because of a 1:1 correspondence with AT episodes, the identification of the AFL episode also operates as a detection of an AT episode. To detect the AFL episode from cardiac activity data 64, in one example, detection logic 66 may be configured to invoke the P-wave morphology feature by, first, P-wave sensing, second, noise sensing, and third, flutter wave sensing. In this manner, detection logic 66 may detect instances of Atrial Flutter waves in cardiac activity data 64 and differentiate those waves from regular P-waves and other cardiac activity of patient 4. As an example criterion for the P-wave morphology feature, a threshold count may be defined for a count of the identified Atrial Flutter waves within a configurable time period of cardiac activity data 64 (e.g., cardiac activity suspected to include an AT episode). Satisfaction of the above p-wave morphology feature criterion may involve detecting a specific number of Atrial Flutter waves (e.g., flutter wave incidents) in cardiac activity data 64 (e.g., of the suspected AT episode) and then, confirming that cardiac activity as an instance of an AFL episode (i.e., True AT episode).

Detection logic 66 may be configured to perform a comparison between the count of Atrial Flutter waves and the threshold count and then, based on the comparison results, generate output data indicating a detection of an AT episode in cardiac activity data 64. Prior to detection logic 66 applying the appropriate set of detection criteria, if cardiac activity data 64 may be suspected of including a cardiac episode, detection logic 66 may confirm that the suspected cardiac activity is a true AT episode.

Satisfaction of an example P-wave morphology criterion may be established in response to a comparison between the count of Atrial Flutter waves and the threshold count; for example, detection logic 66 may determine that the count of Atrial Flutter waves exceeds the threshold count. Detection logic 66 may determine that instead of exceeding the threshold count, cardiac activity data 64 has fewer Atrial Flutter waves and thus, fails to satisfy the example P-wave morphology criterion. In response to determining that the count of Atrial Flutter waves fails to satisfy the p-wave morphology feature criterion, detection logic 66 may classify cardiac activity data 64 as a non-AT episode or a non-episode. Another example P-wave morphology criterion may define a minimum difference between the count of Atrial Flutter waves and the threshold count.

To illustrate by way of example, detection logic 66 may set the threshold count at 13 flutter wave incidents over a 2 minute time period of cardiac activity and then, apply that threshold to a corresponding subset of cardiac activity data 64. If detection logic 66 identifies, from cardiac activity data 64, 13 or more flutter wave incidents within 2 minutes of sensed cardiac activity, detection logic 66 may generate output data indicating a detection of an AT episode. In some examples, detection logic 66 may provide an even more accurate detection by applying a second criterion for the p-wave morphology feature. Detection logic 66 may define a maximum number of detected P-waves for a (true) AT episode; as an example, detection logic 66 establishes 5 P-wave incidents as the maximum number of P-waves for the 2 minute time period of cardiac activity. In the above example where the detection logic 66 identifies 13 or more flutter wave incidents within 2 minutes of the sensed cardiac activity, detection logic 66 may also identify less than 5 P-waves incidents in the same 2 minutes of the sensed cardiac activity and then, generate output data indicating a detection of an AT episode. By employing both criterion for the p-wave morphology feature, the detection of the AT episode is more accurate.

Another feature, herein referred to as "Number of RR Intervals in a specific range (Dynamic range)" feature, is similar to "Number of RR Intervals in a static range" feature except with a dynamic time range as a configurable parameter and may be implemented as an example sub-criteria for Sudden Regularity/Irregularity Onset feature. Like the static feature, a criterion of this feature is configured with a fixed-width (e.g., Median+/−50 ms) range. Besides the median of n (n=12, 24) RR intervals, the median absolute deviation (MAD) of n RR intervals was calculated. Then, instead of Median+/−50 ms range, the Median+/−MAD range was used to count the number of RR intervals before and after a particular beat. When the absolute difference value because the number of RR intervals in 12-beat block Median+/−MAD before and after is more than 40%, the feature may be most effective for the highest number of True AT episodes detection.

As additional feature, herein referred to "Range of difference of RR intervals", is similar to IQR of RR intervals features except that a range of difference of RR intervals (i.e., ΔRR) is computed and then, used to differentiate AT episodes from Non-AT episodes. The range of difference of n (e.g., parameter n=12, 24, or 32) RR intervals before and after a specific beat/RR interval is calculated, computed range values corresponding to n previous RR intervals and n next RR intervals are compared to each other, a resulting difference value from the comparison is further compared with a threshold. This threshold represents a minimum range difference and based on the comparison with the computed range difference, detects True AT episodes. Another parameter may set different values for this threshold (e.g., 95%, 90%, 85%, 80%, 75%) of Median Absolute Deviation (MAD) is another parameter used to differentiate True AT episodes from Non-AT episodes. Similar to Range of difference of RR intervals, MAD may be implemented at different specific heart beats (e.g., 12, 24, 32, or 40) and different difference thresholds (90%, 85%, 80%). True AT episodes may occur for MAD of 32-beat of RR intervals before and after of a specific beat and when the before and after difference threshold is 85% (i.e., 15% of MAD of diff. of RR intervals (Before)>MAD of diff. of RR intervals (After) or 15% of MAD of diff. of RR intervals (After)>MAD of diff. of RR intervals (Before)).

Interquartile range of Difference of RR intervals feature is similar to the IQR criterion of Sudden Regularity/Irregularity feature and may be used to detect True AT episodes. Similar to Sudden Regularity/Irregularity feature, this feature directs a beat block comparison between a n-sized beat block before a specific heart beat interval and another n-sized beat block after the same heart beat interval. In some examples, 12, 16, 24, and 32 are potential beat block sizes and 90%, 85%, 80%, 75% are possible difference thresholds.

Data for Premature Ventricular Contractions (PVCs), which are extra heart beats that begin in one of the heart's two lower pumping chambers (e.g., ventricles), may be used in another possible feature, a PVC feature. PVCs may correspond to a false detection of AT and therefore, identifying PVCs in a suspected episode's data may provide evidence of that the suspected episode is a non-AT episode. PVCs in the form of bigeminy and trigemini may have similar RR intervals patterns as a true AT episode that has ventricle beating in groups and/or patterns. For at least this reason, detection logic 66 (e.g., the decision tree model of FIG. 7) of IMD 10 may be configured to, as a criterion of another possible additional feature, detect a PVC count and then, compare that PVC count to a threshold to determine whether the criterion is satisfied. For instance, given time values for a suspected AT episode, if detection logic 66 determines that an example PVC count within a configurable time range (e.g., 2 minutes) exceeds a pre-determined threshold count, detection logic 66 may generate output data indicative of a non-AT episode (rejecting the suspected AT episode). In examples having the decision tree model of FIG. 7, the above PVC feature may be (logically) configured for the irregular branch.

Further detail regarding the determination of an evidence level of AT episode based on heart beat intervals in the cardiac activity data, the determination that the evidence level indicates relatively regular heart beat intervals or relatively irregular heart beat intervals, and the determination of non-AT episode or an AT episode is provided herein for FIG. 7, which may compute regularity and irregularity measures and determine whether those measures correlate with an AT episode.

FIG. 7 is a flow diagram illustrating an example decision tree to enable detection of an AT episode, in accordance with one or more examples of the present disclosure. The example decision tree represents an example detection analysis for detecting an AT episode based upon patient cardiac activity, in accordance with an evidence level-based feature selection. Other configurations of the example decision tree and other models may be employed for accurate detection of an AT episode.

FIG. 7 is described herein with respect to FIG. 1-2 and according to the illustrated example of FIGS. 1-2, processing circuitry 50 of IMD 10 determines an evidence level of an AT episode based on heart beat intervals in cardiac activity data generated by sensing circuitry 52 of IMD 10 and then, based on the evidence level, determines whether to evaluate the cardiac activity data using a first set of AT detection criteria or a second set of AT detection criteria. In the illustrated example of FIG. 7, processing circuitry 50 of IMD 10 identifies a suspected episode based on patient cardiac activity data generated by sensing circuitry 52 of IMD 10 (210). IMD 10 may rely on a cardiac EGM or ECG for a compatible representation of the patient cardiac activity data from which processing circuitry 50 may identify possible cardiac episode(s). As described herein, there are a number of applicable mechanisms for IMD 10 to utilize in processing the patient cardiac activity data.

Processing circuitry 50 of IMD 10 compares the evidence level to a threshold value and based on that comparison (e.g., is less than 160), selects a branch of the decision tree most likely to result an accurate detection (220). If processing circuitry 50 of IMD 10 determines that the evidence level is less than an example threshold of 160, processing circuitry 50 of IMD 10 proceeds to evaluate RR intervals of the (e.g., suspected) episode using ModeSum/Regularity criteria (230) of regular branch of the decision tree and based on that evaluation, indicates a detection of an AT episode based on satisfaction of the ModeSum/Regularity criteria (YES branch of 230) or proceeds to a next branch level of the decision tree (NO Branch of 230).

The ModeSum/Regularity criteria generally refers to sub-criteria of the first detection criteria for highly regular episodes. Under the ModeSum/Regularity criteria, the sub-criteria may determine, for example, whether more than x % (e.g., x=90) of the RR intervals fall into three bins and if so, whether the greatest bin (by quantity) exceeds y % (e.g., y=50) of the RR intervals in the suspected episode. In some examples, the ModeSum/Regularity criteria does not employ flashback when evaluating the sub-criteria. If the ModeSum/Regularity criteria is satisfied, the episode data is determined to be a true AT episode because of being wave morphology being regular in nature.

If, on the other hand, the patient cardiac activity data (e.g., cardiac EGM) fails to satisfy the above sub-criteria of the first detection criteria, processing circuitry 50 of IMD 10 may proceed to determine whether the RR intervals within a window (e.g., the most recent 120 s) have a median length of less than a threshold length, such as 500 ms (232). If the patient cardiac activity data is determined to have a median of RR intervals (over a 120 s period) less than 500 ms (YES of 232), processing circuitry 50 of 1 MB 10 classifies the patient cardiac activity data as being indicative of a true AT episode. If processing circuitry 50 of IMD 10 determines that the median of the RR intervals is greater than or equal to 500 ms (NO of 232), processing circuitry 50 of 1 MB 10 may proceed to a next branch level along the regular branch at which processing circuitry 50 of IMD 10 is to evaluate the patient cardiac activity data with Sudden Rate Onset/Change feature sub-criteria (234).

The Sudden Rate Onset/Change feature generally refers to sub-criteria of the first detection criteria (e.g., of the decision tree) for determining whether the patient cardiac activity data indicates a sudden change in ventricular rate. The Sudden Rate Onset/Change feature may be a beat-by-beat analysis where processing circuitry 50 of IMD 10 evaluates each heart beat/RR interval with the sub-criteria and if any heart beat/RR interval satisfies the sub-criteria, identifies that heart beat/RR interval as a location of the sudden change in ventricular rate.

In some examples, processing circuitry 50 of IMD 10 determines a first median value (e.g., as amount of time in milliseconds (ms)) of 12-heart beats/RR intervals before a current heart beat/RR interval, a second median value (e.g., as amount of time in milliseconds (ms)) of 12-heart beats/RR intervals after the current heart beat/RR interval, compares the first median value to the second median value, and then, determine whether that comparison is indicative of the sudden change in ventricular rate. In some examples, processing circuitry 50 of IMD 10 computes a difference between the first median value and the second median value and if that difference is greater than a threshold set to 15%, processing circuitry 50 of IMD 10 generates output data indicative of a True AT episode prediction for the patient cardiac activity data.

In response to processing circuitry 50 of IMD 10 determining that the patient cardiac activity data satisfies the Sudden Rate Onset/Change sub-criteria (YES of 234), processing circuitry 50 of IMD 10 classifies the patient cardiac activity data as a True AT episode. If processing circuitry 50 of IMD 10 determines that the patient cardiac activity data does not satisfy the Sudden Rate Onset/Change sub-criteria (NO of 234), processing circuitry 50 of IMD 10 may proceed to a next branch level of the regular branch and evaluate the patient cardiac activity data in view of Atrial Fibrillation (AF) history feature sub-criteria of the first detection criteria (236).

As alternative to following logical flow of the decision tree, processing circuitry 50 of IMD 10 may halt the analysis of the patient cardiac activity data before exhausting all available criteria. In one alternative example, if the above-mentioned difference between the first median value and the second median value is determined to be less than the threshold of 15%, processing circuitry 50 of IMD 10 generates output data indicative of a Non-AT episode classification of the patient cardiac activity data, rejection of the above-mentioned suspected episode as a false positive and/or termination at that branch level in the tree. In some examples, the Sudden Rate Onset/Change sub-criteria utilizes flashback data, which is a history of recent heart beats/RR intervals in the time period preceding suspected episode data in the patient cardiac activity data.

As described herein, the AF history feature may be combined with other features as depicted in the decision tree model of FIG. 7 or, as an alternative, the AF history feature may be applied without other features. In some examples, processing circuitry 50 of IMD 10 may apply one or more criterion of the AF history feature to determine a likelihood probability for AT and if that probability satisfies a threshold probability, generate output data indicative of an accurate determination for a true AT episode. In some instances, the likelihood probability of a true AT episode (or a non-AT episode) may not be sufficiently accurate based on certain standards/metrics (e.g., sensitivity or specificity). In such instances, processing circuitry 50 of IMD 10 may apply one or more other features described herein and compute an updated likelihood probability.

Within a medical device such as IMD 10, depending on the influence of the AF detection on the detection rate for AT episodes (e.g., increasing a sensitivity and/or a specificity), an example criterion of the AF history feature may be determinative regarding whether a suspected episode is a true AT episode. Based on correlations between AF episodes and AT episodes, in general, and IMD 10's detection rate for AF episodes and IMD 10's detection rate for AT episodes, the AF history feature may be configured to accurately classify a patient's cardiac activity data (e.g., cardiac activity data 64 of patient 4 which may be in the form of a cardiac EGM) as a true AT episode, a cardiac episode of another type, or a non-episode. Over a configurable time period, IMD 10 may maintain a history of recoded AF episodes during that period in accordance with the AF history feature. For each recorded AF episode, processing circuitry 50 stores an arrangement of various informational attributes (e.g., a dataset) within memory. Among the various informational attributes in such a history, processing circuitry 50 may store, as examples, AF burden trend, an AF duration, an AF count, a reason for monitoring, among a number of other examples. Further assuming at least a minimum accuracy level for IMD 10's AF episode detection capabilities, the above-mentioned informational attributes may be used to identify false positives/true positives in the patient cardiac activity data, enhancing a current detection rate of IMD 10. One example criterion of the AF history feature sub-criteria defines a minimum threshold duration (e.g., one hour) for an AF episode that, if satisfied within a prior time period, is indicative of a true AT episode.

If the patient cardiac activity data fails to satisfy the Sudden Rate Onset/Change sub-criteria of the first detection criteria, processing circuitry 50 of IMD 10 may apply one or more criterion of the AF history feature to further evaluate cardiac activity data 64. A second example criterion of the AF history feature defines a threshold number (e.g., a minimum) of detected AF episodes over a prior time period. Based on a comparison between the AF count and the above threshold, processing circuitry 50 of IMD 10 may determine that cardiac activity data 64 is indicative of a true AT episode. For instance, if it is determined that IMD 10 recorded at least the threshold number of AF episodes over the prior time period, processing circuitry 50 of IMD 10 generates output data indicative of a true AT episode in patient 4's cardiac activity data 64. In some examples, having the AF count be fewer than the threshold may be indicative of a non-AT episode. In other examples, the comparison between the AF count and the threshold is not dispositive, and further evaluation may be needed.

Based on a determination, by processing circuitry 50 of IMD 10, that cardiac activity data 64 satisfies the AF history feature sub-criteria of the first detection criteria (YES of 236), processing circuitry 50 of IMD 10 may classify the patient cardiac activity data as a true AT episode. If processing circuitry 50 of IMD 10 determines that the AF history feature sub-criteria has not been satisfied by the patient cardiac activity data (NO of 236), processing circuitry 50 of IMD 10 may proceed to a last branch level along the regular branch of the decision tree and identify logic to execute in accordance with a P-wave morphology feature (238). To benefit IMD 10 and the patient, processing circuitry 50 implements the P-wave Morphology feature to differentiate Atrial Flutter waves from regular P-waves, further improving upon IMD 10's detection capabilities. In some examples, the P-wave morphology feature (which may also be known as the P-wave Morphology atrial flutter feature) defines one or more criterion that processing circuitry 50 employs when evaluating the patient cardiac activity data for Atrial Flutter waves.

Based on a determination that the Atrial Fibrillation (AF) history feature sub-criteria of the first detection criteria is not satisfied, processing circuitry 50 of IMD 10 may conclude the regular branch of the decision tree with the one or more criterion of the P-wave Morphology feature. Based on an evaluation of the patient cardiac activity data 64, processing circuitry 50 of IMD 10 may determine whether a count of Atrial Flutter waves satisfies the P-wave morphology feature sub-criteria of the first detection criteria. The P-wave morphology feature sub-criteria of the first detection criteria may be considered satisfied, for example, if processing circuitry 50 identifies at least a threshold count in a number of Atrial Flutter waves over a configurable time period. In such a case, processing circuitry 50 may generate, as a final classification, output data indicative of a true AT episode (YES of 238). On the other hand, processing circuitry 50 of IMD 10 may have exhausted the first detection criteria if the P-wave morphology feature is not satisfied, for example, if the patient cardiac activity data includes fewer than the threshold number of Atrial Flutter waves. In that case, the suspected episode most likely cannot be a true AT episode, and processing circuitry 50 of IMD 10 may generate output data indicating that the patient's cardiac activity data is indicative of a non-AT cardiac episode or a non-episode (NO of 238). Given a lack of remaining criteria to evaluate, processing circuitry 50 may terminate further processing of the patient cardiac activity data. In some examples, processing circuitry 50 generates output data indicative of a rejection of the suspected episode.

With respect to the above term "flashback", the present disclosure refers to data (e.g., R-peak locations) corresponding to any additional cardiac activity (e.g., RR interval(s))

that occurred prior to the cardiac EGM data and/or a start time of a suspected AT episode. Time values and other flashback data for any one of the additional RR intervals may accompany the suspected episode data in the cardiac EGM. As an option, IMD 10 or a similar medical device may store flashback data for a select number of episodes. Episode data for a normal episode may span a 2 minute period (i.e., 120 seconds) that is followed or preceded by flashback data for associated RR intervals (i.e., a flashback episode). RR intervals for an example flashback episode may occupy an 8 minute period that is followed by a 2 minute period of RR intervals and other EGM activity. Some of the features described herein (e.g., Sudden rate onset criteria) apply only to RR intervals and thus, may take advantage of flashback data to further improve upon IMD 10's performance. Nonetheless, for any feature described herein to operate properly, flashback data is not necessary, and the option to store such flashback data may either inactive or, if active, omitted from any transmission of cardiac EGM data. Alternatively, IMD 10 may maintain a (running) history of RR intervals for the patient and use that history when evaluating the suspected episode data for a true AT episode.

For an evidence level equal to or higher than the threshold value, the patient cardiac activity data (e.g., a cardiac EGM) is analyzed under an irregular branch of the decision tree depicted in FIG. 7. As described herein, processing circuitry 50 of IMD 10 compares the evidence level to the above threshold value (e.g., 160) and based on the comparison, directs the detection analysis of the patient cardiac activity data to a set of detection criteria configured to produce a reliable AT detection (220). If the comparison results demonstrate that the evidence level is greater than the threshold value (e.g., 160) (NO of 220), processing circuitry 50 of IMD 10 applies second detection criteria as depicted in the irregular branch. Depending on the patient cardiac activity data and its evidence level, one set of criteria may be more effective than another set of criteria with respect to AT detection. Features of the second detection criteria may be tailored to a certain level of irregularity/regularity as denoted by the above threshold evidence level, and compared to the first detection criteria and/or other criteria, the second detection criteria may be most likely to return an accurate classification of the suspected episode as either a True AT episode or a non-AT episode.

At an initial level of the irregular branch, processing circuitry 50 of IMD 10 proceeds to evaluate the patient cardiac activity data using T-Wave Oversensing (TWOS) Rejection sub-criteria (240) and if the TWOS rejection sub-criteria is satisfied (YES of 240), processing circuitry 50 of IMD 10 generates output that indicates T-Wave oversensing (i.e., a T-Wave Oversensing (TWOS) episode) and a rejection of the patient cardiac activity data as a True AT episode. Processing circuitry 50 of IMD 10 may determine that the TWOS sub-criteria is satisfied, for example, by determining, from available cardiac activity data, a number of heart beat intervals where each heart beat interval is less than a configurable time value, identifying, in the number of heart beat intervals, at least one heart beat interval that is less than a pre-determined percentage of a next heart beat interval and a pre-determined percentage of a previous heart beat interval, and then, determining whether the at least one heart beat interval exceeds a pre-defined threshold number. In such a case where the patient cardiac activity data is depicting an episode considered to be a TWOS episode, processing circuitry 50 of IMD 10 may reject the patient cardiac activity data without proceeding further down the irregular branch. Based on a determination of non-satisfaction of the TWOS rejection sub-criteria (NO of 240), processing circuitry 50 of IMD 10 applies a criterion associated with a next feature of the irregular branch of the decision tree.

After confirming a lack of T-wave oversensing satisfying the TWOS rejection sub-criteria, processing circuitry 50 of IMD 10 proceeds to apply High Heart Rate sub-criteria (242) (e.g., whether more than X % of RR intervals are less than 400 ms where X is a percentage value can vary from 51% to 60% or 65%). If the patient cardiac activity data passes the high heart rate sub-criteria (YES of 242), processing circuitry 50 of IMD 10 classifies the patient cardiac activity data as a true AT episode. However, if processing circuitry 50 of IMD 10 determines that the patient cardiac activity data 64 does not satisfy the high heart rate sub-criteria (NO of 242), the Sudden Rate Onset sub-criteria is invoked (244).

In some examples, processing circuitry 50 of IMD 10 applies the same or similar Sudden Rate Onset sub-criteria as applied for regular branch of the decision tree. If any heart beat/RR interval satisfies the sub-criteria (YES of 244), processing circuitry 50 of IMD 10 identifies that heart beat/RR interval as a location of the sudden change in ventricular rate and then, generates output that indicates patient cardiac activity data as being a True AT episode. If, on the other hand, processing circuitry 50 of IMD 10 fails to identify one or more heart beats/RR intervals corresponding to the sudden change in ventricular rate (NO of 244), processing circuitry 50 of IMD 10 applies Sudden Regularity/Irregularity Onset sub-criteria by performing an interquartile range (IQR) check of heart beats/RR intervals at every heart beat or, alternatively, at every $N^{th}$, e.g., $32^{nd}$, heart beat (246). As described herein, the IQR check may accompany other criterion to form the Sudden Regularity/Irregularity Onset sub-criteria.

If processing circuitry 50 of IMD 10 determines that the patient cardiac activity data passes the Sudden Regularity/Irregularity Onset sub-criteria (YES of 246), the patient cardiac activity data is considered a true AT episode. However, if the patient cardiac activity data does not pass the Sudden Regularity/Irregularity Onset sub-criteria, the patient cardiac activity data is rejected as an AT episode and/or classified as a non-AT episode/non-episode or, as an option, is further evaluated with additional criteria. In some examples where processing circuitry 50 of IMD 10 determines that the patient cardiac activity data does not satisfy the Sudden Regularity/Irregularity Onset sub-criteria (NO of 246), processing circuitry 50 of IMD 10 may proceed to apply the AF History feature sub-criteria of the second detection criteria (248).

Processing circuitry 50 of IMD 10 may apply the same or similar AF History sub-criteria as applied for the regular branch of the decision tree. The AF history features uses the patient's history of detected AF episodes as evidence of a higher likelihood of True AT. In some examples, processing circuitry 50 may analyze historical AF episodes for indicia of a true AT episode and if that indicia also correlates with the suspected episode, processing circuitry 50 may consider the AF History feature satisfied (YES of 248). The AF History feature is not satisfied (NO of 248), for example, if processing circuitry 50 determines that the suspected episode does not include sufficient indicia for the true AT episode and proceeds to the P-wave morphology feature (250). The P-wave Morphology feature is a last feature along the irregular branch and may be used to differentiate Atrial Flutter waves from regular P-waves.

In some examples, processing circuitry 50 determines how many Atrial Flutter waves (if any) are included in the patient cardiac activity data and if that Atrial Flutter wave count exceeds a threshold count, the P-wave morphology feature is considered satisfied, and the suspected episode is classified as a true AT episode (YES of 250). In other examples, processing circuitry 50 may determine that the P-wave morphology feature is not satisfied in response to a determination that the Atrial Flutter wave count fails to exceed or at least meet the threshold count and in turn, generate output data classifying the suspected episode of the patient cardiac activity data as a non-AT episode or a non-episode (NO of 250). Processing circuitry 50 may determine that the P-wave morphology feature is not satis-fied and, in particular, that the count of Atrial Flutter waves in cardiac activity data 64 fails to satisfy the p-wave mor-phology feature criterion. In some examples, processing circuitry 50 generates output data indicative of a rejection of the suspected episode. Given a lack of another criterion to evaluate, processing circuitry 50 may terminate further processing of the patient cardiac activity data and conclude the detection analysis of the suspected episode. In some examples, processing circuitry 50 of IMD 10 proceeds to one or more optional criterion as a last feature of the decision tree.

A number of additional features may be incorporated into the irregular branch of decision tree depicted in FIG. 7. One possible feature, "No. of RRints in static range", is an optional criterion that increases sensitivity and/or specificity. If the patient cardiac activity data does not satisfy the Sudden Regularity/Irregularity Onset sub-criteria, process-ing circuitry 50 of IMD 10 further evaluates the patient cardiac activity data by computing a number of heart beats/ RR intervals in a static range (e.g., Median+/−50 ms) and then, determining whether the number of heart beats/RR intervals satisfies a threshold number. If processing circuitry 50 of IMD 10 determines that the number of heart beats/RR intervals exceeds the threshold, processing circuitry 50 of IMD 10 classifies the patient cardiac activity data as a True AT episode. If processing circuitry 50 of IMD 10 determines that the number of heart beats/RR intervals fails to exceed the threshold, processing circuitry 50 of IMD 10 classifies the patient cardiac activity data as a Non-AT episode.

As an optional feature, the "Number of RRints in static range" sub-criteria may not be executed even if other criterion of second set of detection criteria fail. Alterna-tively, detection logic 66 may extend the decision tree model with one or more other features. By adding and/or removing features, the decision tree model's detection rate increases because (even when applied independently) both features significantly improve overall True AT detection perfor-mance.

As another optional feature, the Premature Ventricular Contraction (PVC) feature sub-criteria may include a crite-rion directed to determining, from cardiac activity data 64, a PVC count for a configurable time period and then, determining, based on a comparison between the PVC count to a threshold count, satisfaction of the PVC criterion. Satisfaction of the PVC criterion indicates that the likeli-hood of an AT episode is considerably low, and the suspected AT episode most likely is a non-AT episode instead of a true AT episode. Given that the RR intervals of episodes with PVCs may be easily confused for AT episodes, there is a correlation between PVC count and non-AT episodes that the PVC feature leverages to confirm or reject the suspected AT episode. If, for instance, patient 4 is determined to have an excessive number of PVCs, those PVCs probably caused the false AT episode detection.

Processing circuitry 50 of IMD 10 may execute detection logic 66 to compute an initial probability that cardiac activity data 64 and while running, detection logic 66 may apply sub-criteria of each feature and update that probability in view of at least one applied criterion. For instance, after applying the PVC criterion to determine that a PVC count of cardiac activity data 64 exceeds the above threshold count, processing circuitry 50 of IMD 10 decreases the running probability. If the PVC count of cardiac activity data 64 falls below the above threshold count, processing circuitry 50 of IMD 10 may increase the above probability to account for the increased likelihood that the suspected episode is a true AT episode and/or increase a second probability of a differ-ent episode type or for the suspected episode of being a non-episode or noise.

The order and flow of the operation illustrated in FIGS. 6 and 7 are examples. In other examples according to this disclosure, more or fewer sub-criteria may be considered. Further, in some examples, processing circuitry may per-form or not perform the methods of FIG. 6 and FIG. 7, or any of the techniques described herein, as directed by a user, e.g., via external device 12 or computing devices 100. For example, a patient, clinician, or other user may turn on or off functionality for identifying changes in patient health (e.g., using Wi-Fi or cellular services) or locally (e.g., using an application provided on a patient's cellular phone or using a medical device programmer).

Figure 8:
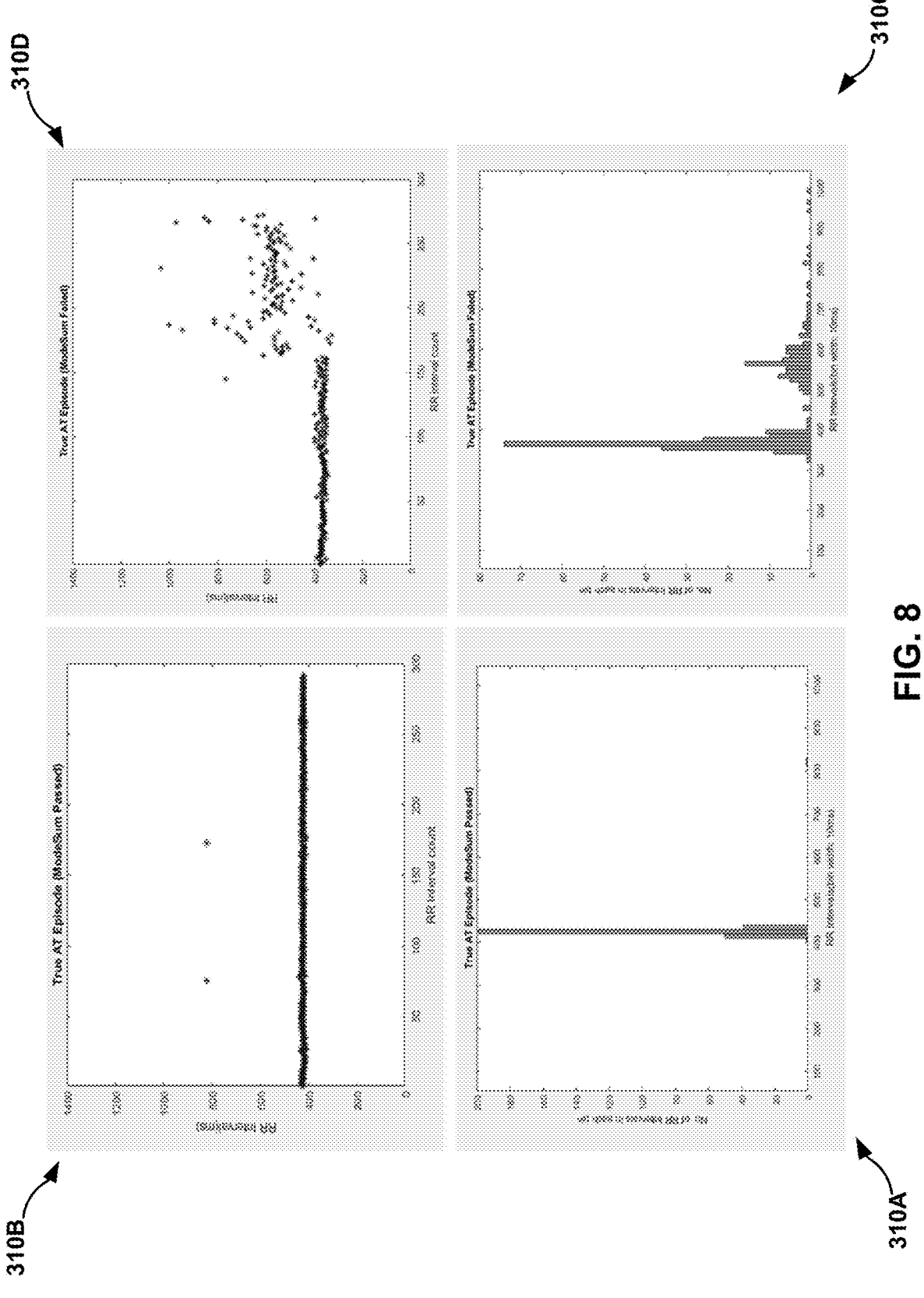
FIG. 8 depicts four graphs, each illustrating an application of ModeSum sub-criteria as part of a set of detection criteria for an AT episode, in accordance with one or more examples of the present disclosure.

FIGS. 8-12 present graphical embodiments of some of the features employed in the decision analysis. FIG. 8 depicts four graphs 310A-D, each illustrating an application of sub-criteria for ModeSum feature as part of a set of detection criteria for an atrial tachycardia (AT) episode, in accordance with one or more examples of the present disclosure. Graphs 310A and 310B belong to one patient while graphs 310C and 310D belong to another patient and each depict an aspect of different sub-criteria for the ModeSum feature.

When an evidence level for the cardiac activity data indicates a wave morphology that is regular in nature, the ModeSum/Regularity feature is applied to determine whether the cardiac activity data indicates a true AT episode based on a particular level of regularity for the heart beat intervals over the pre-determined time period. The ModeSum/Regularity feature includes a criterion that sets a configurable time range for a first threshold percentage of a number of the heart beat intervals. The criterion further sets a pre-determined portion of the configurable time range to includes a second threshold percentage of the heart beat intervals. In one example, satisfying the above criterion may involve determining when x % (e.g., x=97, 95, 90, 85, or 80) of heart beat intervals (e.g., time values between R-waves) are within three bins (e.g., where each bin's width is 10 ms) and/or more than n % (e.g., n=70, 65, 60, or 51) of all heart beat intervals are in one bin (i.e., Mode bin).

Each of graphs 310A-B and graphs 310C-D depicts an example application of ModeSum/Regularity feature on cardiac activity data representing two different distributions of heart beat or RR intervals. Each of graphs 310A-D include text to indicate a detection of an AT episode or a non-AT episode and results from applying the feature's sub-criteria for the ModeSum/Regularity feature. Graph 310A and Graph 310C depict histograms where each histo-gram includes three bins for each of the above two distri-butions. Graph 310A depicts three bins (e.g., Mode, 2nd highest, and 3rd highest) spanning 30 ms in total (e.g., the configurable time range) and including more than 90% (e.g., the first threshold percentage) of the heart beats in the corresponding distribution. In graph 310A, a middle (or Mode) bin (e.g., the configurable time range) represents more than 50% (e.g., the second threshold percentage) of the heart beats in the corresponding distribution. Graph 310B depicts a plot of RR intervals for the distribution of graph 310A, which demonstrates that 90% of the distribution fall into a 30 ms time range spanning three bins and further demonstrates that the Mode bin (e.g., the pre-determined portion) of the three bins (e.g., of the configurable time range) exceeds the second threshold percentage. Hence, Graphs 310A and 310B depict cardiac activity that is determined to be a true AT episode.

In contrast, Graph 310C and graph 310D demonstrate that there isn't a similar 30 ms time range that includes more than 90% of the corresponding distribution. A configurable parameter that may modify the application of the ModeSum/Regularity feature is a flashback. It should be noted that graphs 310C and 310D depict a failure of the sub-criteria; for the cardiac EGMs represented by these histograms, another feature, such as Sudden Rate Onset, detects the true AT.

Figure 9:
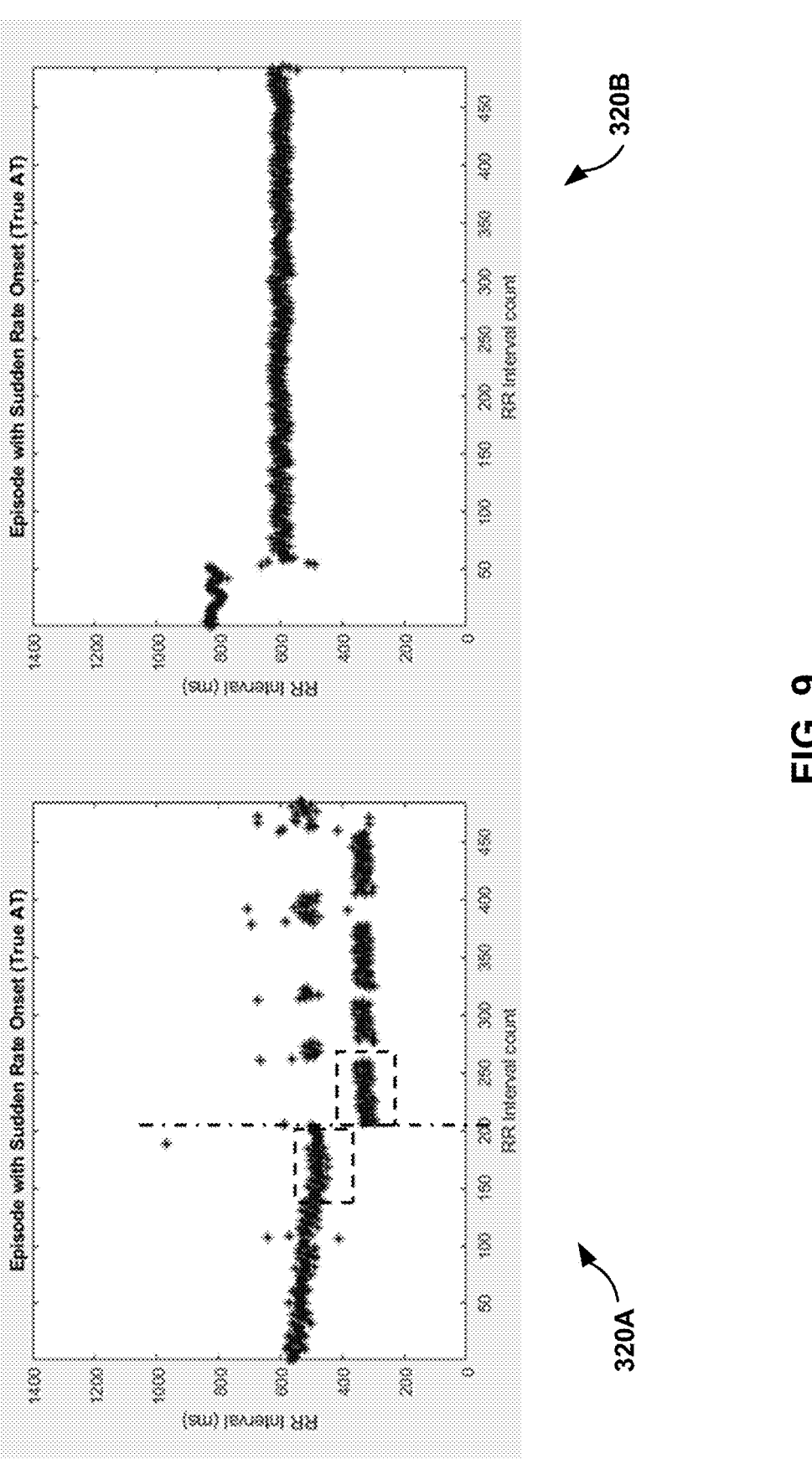
FIG. 9 depicts two graphs, each illustrating an application of Sudden Rate Onset sub-criteria as part of a set of detection criteria for an AT episode, in accordance with one or more examples of the present disclosure.

FIG. 9 depicts two graphs, each illustrating an application of sub-criteria for Sudden Rate Onset feature as part of a set of detection criteria for an atrial tachycardia (AT) episode, in accordance with one or more examples of the present disclosure.

As described herein, the Sudden Rate Onset feature may be implemented in a model (e.g., a decision-tree model) that includes a first set of criteria and a second set of criteria. The Sudden Rate Onset feature generally identifies AT episodes based on a ventricular rate, in particular, a change in ventricular rate over a pre-determined number of heart beat intervals. The Sudden Rate Onset feature achieves a high accuracy level when applied to cardiac activity data having either a particular level of irregularity or a particular level of regularity, for example, as defined by evidence level.

The Sudden Rate Onset feature is a beat-by-beat analysis of cardiac episode data for a pre-determined time period. For each heart beat in the cardiac episode data, a criterion is evaluated against median time values for n heart beats and n heart beats after that heart beat, where n is a configurable parameter denoting the above pre-determined number of heart intervals. The change in ventricular rate criterion may include a threshold set to a difference value between the above median time values of the above pre-determined number of heart intervals before and after a specific heart beat interval. If, at the specific heart beat interval, the difference value exceeds the threshold in satisfaction of the criterion, the cardiac episode data indicates a true AT.

The criterion may utilize the threshold, as defined by the above difference value, as a minimum change in ventricular rate for the Sudden Rate Onset feature. Cardiac episode data that indicates a substantial change in ventricular rate involves a larger difference value between a median of n (e.g., n=8, 12, 16, or 24) heart beat intervals before and after a specific interval. Graph 320A and graph 320B depict true AT episodes where the above criterion is satisfied by each graph's corresponding cardiac activity data. Graph 320A depicts by way of dashed lines intersecting at a current beat of beat 200, boxes for a previous 12-beat block and a next 12-beat block; medians time values for each 12-beat block are computed and then, compared with each other to produce a difference value that exceeds an example threshold (e.g., 15%).

The Sudden Rate Onset feature sub-criteria may be further configured in accordance with various parameters. For instance, flashback may be employed when comparing median time values of adjacent beat blocks. Instead of a beat-by-beat analysis, another parameter may configure the above sudden change in ventricular rate criterion to apply with 50% window overlapping techniques.

Figure 10:
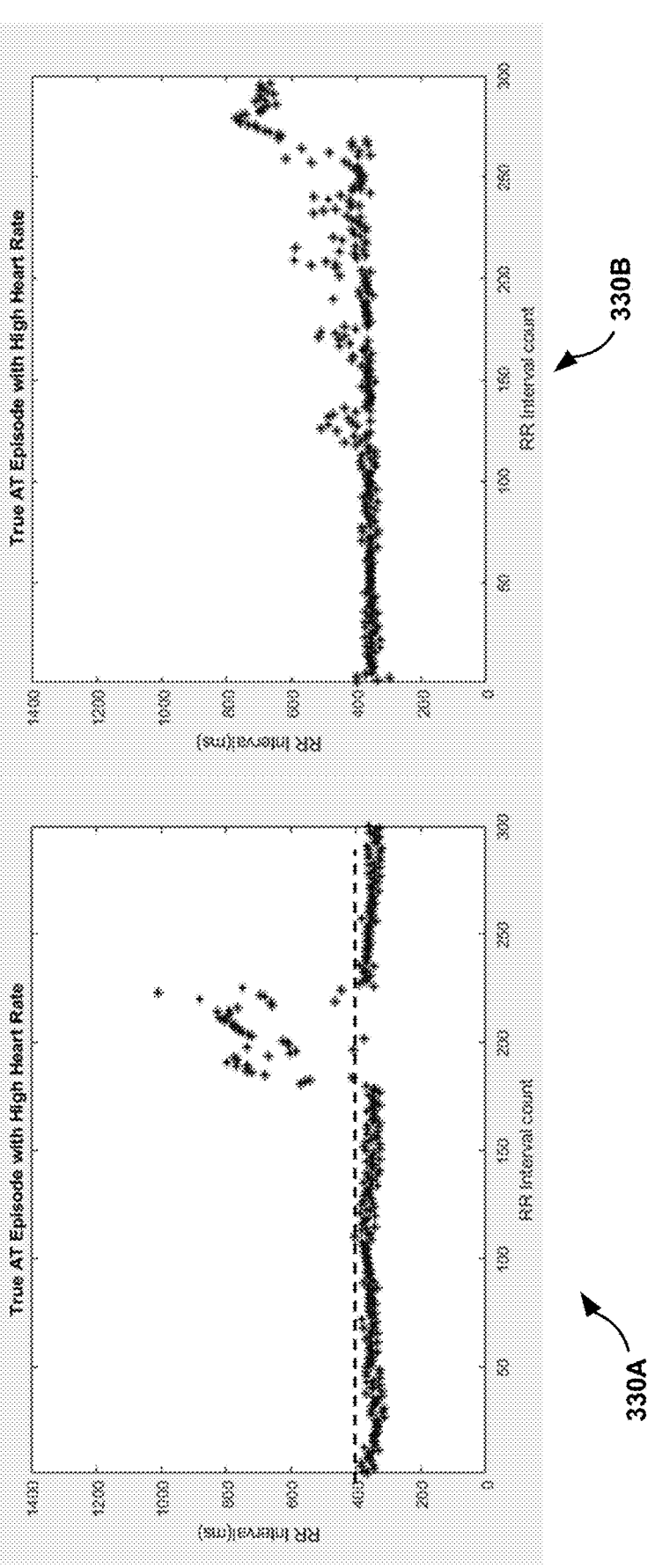
FIG. 10 depicts two graphs, each illustrating an application of High Heart Rate sub-criteria as part of a set of detection criteria for an atrial tachycardia (AT) episode, in accordance with one or more examples of the present disclosure.

FIG. 10 depicts two graphs, each illustrating an application of High Heart Rate sub-criteria as part of a set of detection criteria for an atrial tachycardia (AT) episode, in accordance with one or more examples of the present disclosure.

Graph 330A and graph 330B depict cardiac activity data as distributions of time data for heart beat intervals over a pre-determined time period. Each graph plots a time value for each heart beat interval representing an amount of time between R-waves. Each of graph 330A and graph 330B depict a true AT episode that is detected based on evaluation of sub-criteria for a High Heart Rate feature. As described herein, the High Heart Rate feature may be implemented in a model (e.g., a decision-tree model) that includes a first set of criteria and a second set of criteria. The High Heart Rate feature generally identifies AT episodes based on heart rate (e.g., a proportion of total time) and achieves a high accuracy level when applied to cardiac activity data having a particular level of irregularity.

To illustrate an example criterion of the High Heart Rate feature, graphs 330A further depicts a dashed line to demark a particular time value for a high heart rate. Consecutive heart beat intervals below the particular time value indicate an equivalent heart rate that is consider higher than average. If a sufficient amount of cardiac activity data is below the particular time value, the High Heart Rate feature is satisfied and the cardiac activity data indicates true AT episode. The example criterion may define, as a first threshold, a minimum amount of time for the cardiac activity to suffice as a true AT episode; for example, the first threshold may include a number or a proportion of the (e.g., total number of) heart beat intervals that stay within the particular time value. A second threshold may include the particular time value and/or a pre-determined time range for the first threshold number or proportion of the heart beat intervals.

Because a substantial percentage of the RR intervals of each graph 330A and graph 330B satisfy the High Heart Rate feature, both graphs depict true AT episodes with High Heart Rate by way of an example application of detection criteria for true AT episodes as described herein. Graph 330A, in particular, illustrates a true AT episode with a heart rate of 150 bpm denoted by a dashed line at 400 ms of which a majority (e.g., greater than 50% or 51% and up) of RR Intervals do not exceed. The present disclosure provides additional examples of this feature.

Figure 11:
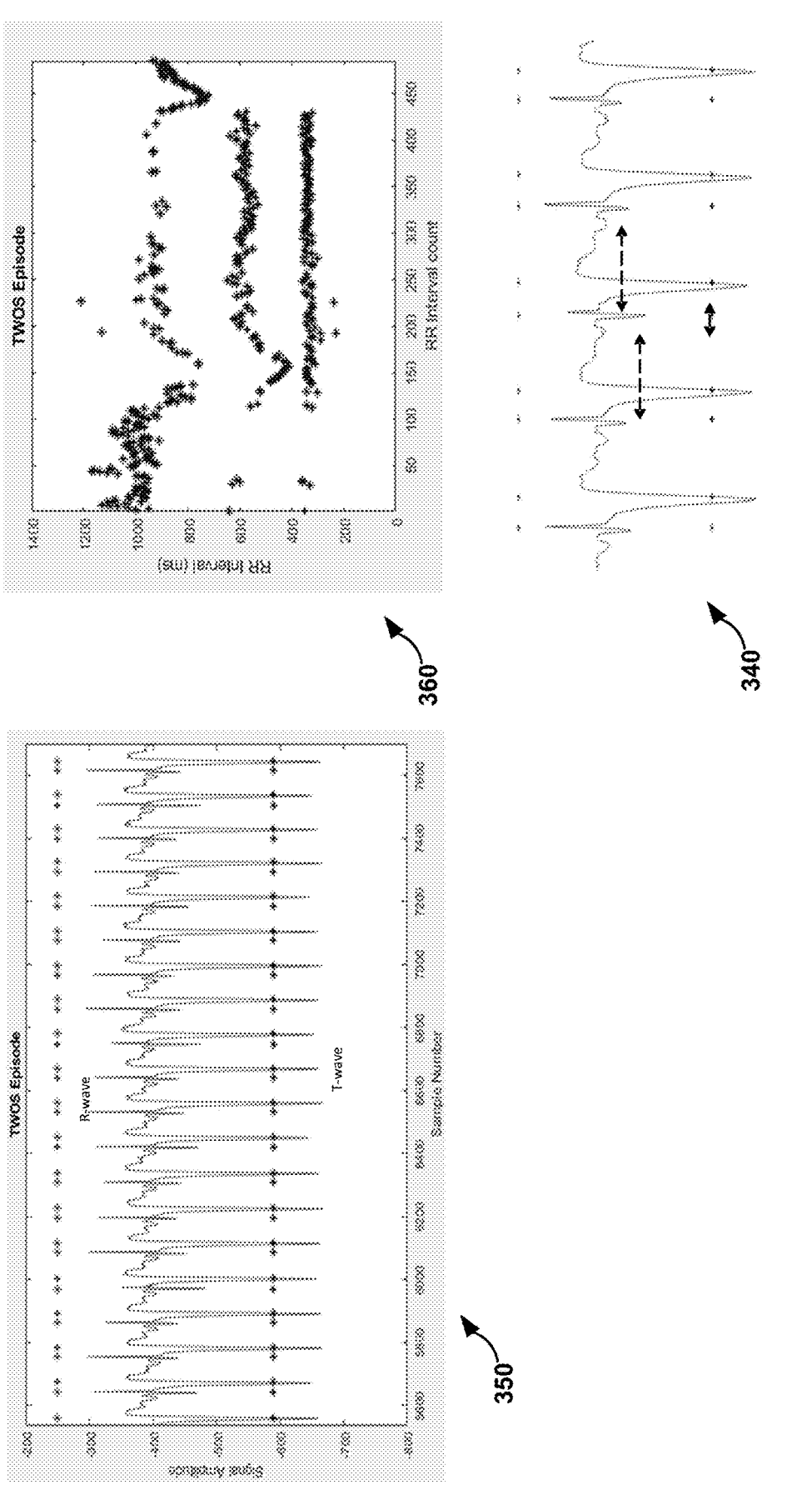
FIG. 11 depicts three graphs, each illustrating an application of T-wave oversensing sub-criteria as part of a set of detection criteria for an atrial tachycardia (AT) episode, in accordance with one or more examples of the present disclosure.

FIG. 11 depicts three graphs, each illustrating an application of T-wave Oversensing (TWOS) Rejection feature sub-criteria as part of a set of detection criteria for an atrial tachycardia (AT) episode, in accordance with one or more examples of the present disclosure.

Graphs 340, 350, and 360 include text to identify as a TWOS episode and each depicts some aspect of cardiac activity data and respective sub-criterion for rejecting TWOS episodes as non-AT. As described herein, the TWOS rejection feature may be implemented in a model (e.g., a decision-tree model) that includes a first set of criteria and a second set of criteria. By rejecting TWOS episodes as non-AT episodes, the model may reduce a false positive rate of the first set of criteria and the second set of criteria. The TWOS rejection feature generally identifies non-AT episodes based on T-wave oversensing signals and achieves a high accuracy level when applied to cardiac activity data having a particular level of irregularity.

Example sub-criteria for an example method for TWOS episode detection includes a first criterion, a second criterion, and a third criterion. The first criterion is directed to determining, from the cardiac activity data, a number of heart beat intervals where each heart beat interval is less than a configurable time value. The second criterion is directed to identifying, in the number of heart beat intervals, at least one heart beat interval that is less than a pre-determined percentage of a next heart beat interval and a pre-determined percentage of a previous heart beat interval. The third criterion is directed to determining whether the at least one heart beat interval exceeds a threshold number.

For each identified heart beat interval (which is denoted as RR(n)) less than 360 ms (RR(n)), a previous heart beat interval (RR(n−1)) immediately before that heart beat interval (RR(n)) and a next heart beat interval (RR(n+1)) satisfies the first criterion by exceeding that identified heart beat interval's time value by a pre-determined amount (e.g., at least 33%). If, within a pre-determined time period (e.g., 120 seconds) of the cardiac activity data, at least the above threshold number (e.g., 20) of heart beat intervals satisfy the first criterion, the second criterion also is satisfied. The above TWOS sub-criterion may be represented as mathematical expression RR(n)<0.75*RR(n+1) and RR(n) <0.75*RR(n−1)) (i.e., RR(n)<0.75*RR(n+1) and RR(n) <0.75*RR(n−1)).

Graph 340 indicates a heart beat RR interval n that is less than 75% of a previous RR interval (i.e., n−1) and 75% of a next RR interval (i.e., n+1). Graph 350 indicates more than 20 instances of the above RR interval n. Graph 360 indicates a RR interval of less than 360 ms. In some examples, sub-criteria for T-wave oversensing (TWOS) and High Heart Rate features may only be used for confirming/rejecting suspected episodes with AT Evidence greater than or equal to 160.

As demonstrated in FIG. 11, it is very unlikely that an episode is a true AT after sensing more than 25% change in heart beat intervals before and after a specific heart beat interval (RR(n)) for a substantial proportion of the captured cardiac activity. Therefore, identifying and rejecting non-AT episodes may reduce a probability of a false detection as a true AT episode. There are a number of configurable parameters for modifying the TWOS sub-criteria including the pre-determined time period of a suspected episode. The present disclosure provides examples of this feature.

Figure 12:
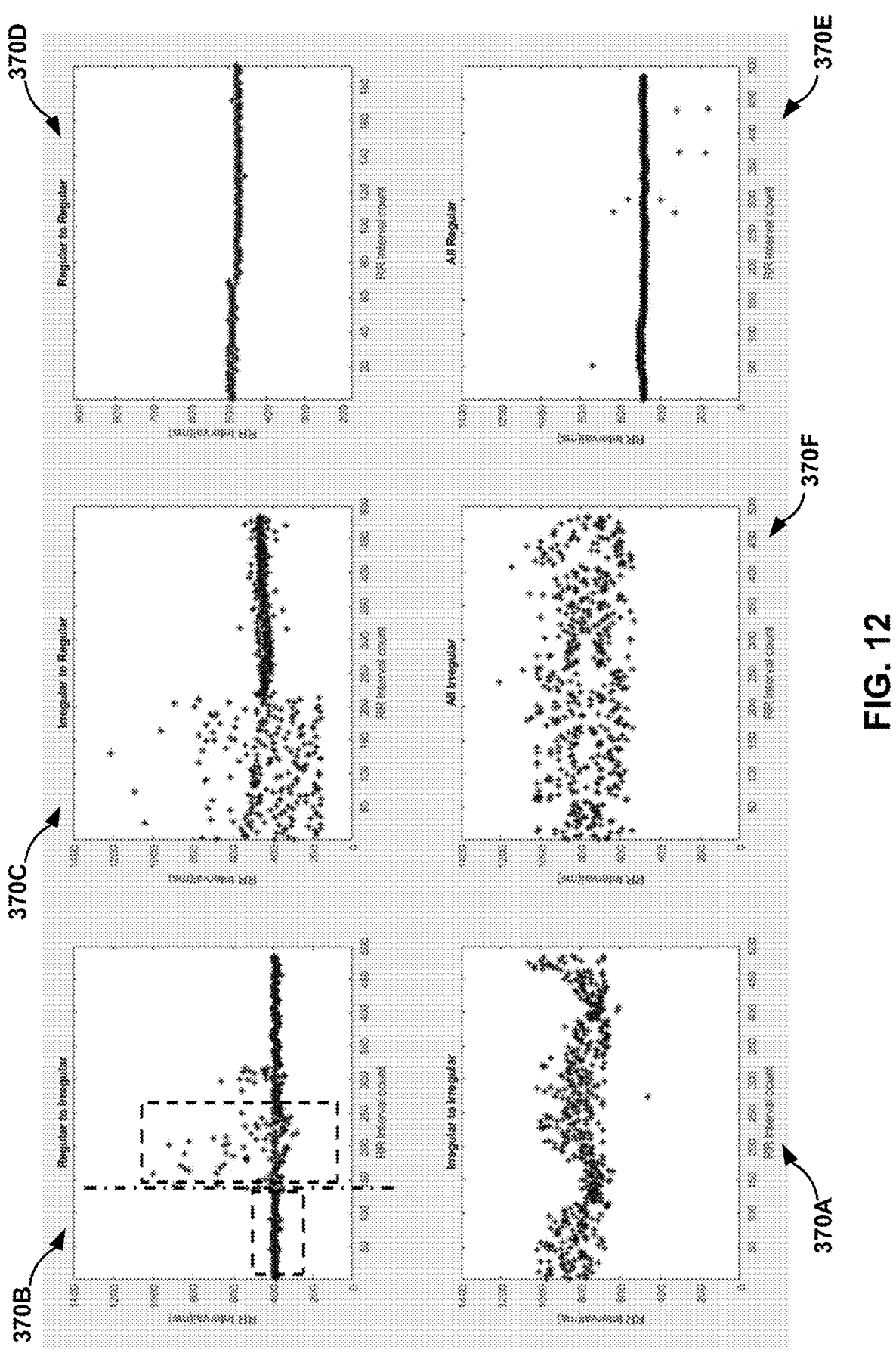
FIG. 12 depicts six graphs, each illustrating an application of Sudden Regularity/Irregularity Onset sub-criteria as part of a set of detection criteria for an atrial tachycardia (AT) episode, in accordance with one or more examples of the present disclosure.

FIG. 12 depicts six graphs, each illustrating an application of Sudden Regularity/Irregularity Onset feature sub-criteria as part of a set of detection criteria for an atrial tachycardia (AT) episode, in accordance with one or more examples of the present disclosure.

The Sudden Regularity/Irregularity Onset feature includes sub-criteria for the Interquartile range (IQR) check described herein, which may include a criterion setting a threshold for an interquartile range of n (e.g., n=12, 24, or 32) heart beats/RR intervals before and after a specific heart beat/RR interval where n is a parameter (e.g., configurable parameter) for setting a beat block size. The beat block size refers to a configurable range of heart beat intervals for the IQR check. IQR generally refers to a measure of statistical dispersion, being equal to the difference between 75th and 25th percentiles, for example, where the IQR is the first quartile subtracted from the third quartile. According to the IQR check, the threshold for the second criterion may be compared with time data corresponding to one or both IQRs of n heart beats/RR intervals, and if the time data satisfies (e.g., exceeds) the threshold, the specific heart beat/RR interval most likely corresponds to a transition from regular-to-irregular or irregular-to-regular. By "time data", the present disclosure may refer to time values for amounts or lengths of time, for example, in terms of seconds or milliseconds.

In some examples, the IQR check defines the threshold for the second criterion as a difference between time values of a preceding IQR and a succeeding IQR of the specific heart beat/RR interval. If the difference of IQR time values is computed and determined to exceed a fixed percentage parameter (e.g., 70%, 80%, or 90%), the specific heart beat/RR interval may be considered an onset of regularity or irregularity. Given a distribution (e.g., a histogram) of a suspected AT episode indicative of an irregular evidence level, the IQR check may be satisfied if an absolute value of the difference of IQRs before and after at least one heart beat/RR interval in the box plot exceeds 90%, for example, if 10% of the IQR of RR intervals before the specific heart beat/RR interval is greater than the IQR of RR intervals after the specific heart beat/RR interval or if 10% of the IQR of RR intervals after the specific heart beat/RR interval is greater than the IQR of RR intervals before the specific heart beat/RR interval.

Each of graphs 370A-F depict RR intervals plot of episodes and, in particular, graph 370A depicts an example application of Sudden Regularity/Irregularity Onset on data representing a distribution of heart beat interval time information (e.g., time between R-waves). Each of Graphs 370A-F represents a different permutation that could be depicted by comparing RR interval times of 32-beat blocks: irregular-to-irregular, regular-to-irregular, irregular-to-regular, regular-to-regular, all regular, and all irregular. The 32-beat blocks are illustrated as dashed lines in graph 370A. Examining an interquartile range of 32-beats before and 32-beats after a current heart beat determines which permutation. As a second sub-criterion, if a difference between the 32-beat blocks is greater than 90%, an onset of (sudden) regular/irregular is detected.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical system comprising:
a plurality of electrodes configured to sense cardiac activity of a patient;
sensing circuitry configured to provide cardiac activity data based on the sensed cardiac activity, the cardiac activity data including at least one of electrogram (EGM) data or electrocardiogram (ECG) data; and
processing circuitry configured to:
    determine an evidence level of an atrial tachycardia (AT) episode of the patient based on heart beat intervals in the cardiac activity data over a pre-determined time period;
    determine the evidence level indicates relatively regular heart beat intervals over the pre-determined time period in response to the evidence level corresponding to relatively regular heart beat intervals;
    determine the evidence level indicates relatively irregular heart beat intervals over the pre-determined time period in response to the evidence level corresponding to relatively irregular heart beat intervals;
    based on the determination that the evidence level indicates relatively regular heart beat intervals over the pre-determined time period:
        apply, to the cardiac activity data, a first set of AT detection criteria; and
        indicate a detection of the AT episode based on satisfaction of at least one of the first set of AT detection criteria; and
    based on the determination that the evidence level indicates relatively irregular heart beat intervals over the pre-determined time period:
        apply, to the cardiac activity data, a second set of AT detection criteria, the second set of AT detection criteria including at least one criterion different from the first set of AT detection criteria; and
        indicate a detection of the AT episode based on satisfaction of at least one of the second set of AT detection criteria; and
    communication circuitry configured to transmit data comprising an indication of the detection of the AT episode to a computing device, wherein the processing circuitry controls the communication circuitry to transmit the data.

2. The medical system of claim 1, comprising an implantable medical device that comprises a housing, the plurality of electrodes positioned on the housing, the sensing circuitry, the communication circuitry, and the processing circuitry, the housing and the electrodes configured for subcutaneous implantation.

3. The medical system of claim 1, wherein the cardiac activity data include cardiac EGM data, and the processing circuitry is configured to:
determine at least one regularity measure of R-waves in the cardiac EGM data over the pre-determined time period and at least one irregularity measure of the R-waves in the cardiac EGM data over the pre-determined time period; and
determine the evidence level of the atrial tachycardia (AT) episode based on the at least one regularity measure of R-waves in the cardiac EGM data over the pre-determined time period and the at least one irregularity measure of the R-waves in the cardiac EGM data over the pre-determined time period.

4. The medical system of claim 1, wherein the second set of AT detection criteria comprises T-wave oversensing sub-criteria comprising a first criterion, a second criterion, and a third criterion, wherein the first criterion is directed to determining, from the cardiac activity data, a number of heart beat intervals where each heart beat interval is less than a configurable time value, wherein the second criterion is directed to identifying, in the number of heart beat intervals, at least one heart beat interval that is less than a pre-determined percentage of a next heart beat interval and a pre-determined percentage of a previous heart beat interval, wherein the third criterion is directed to determining whether the at least one heart beat interval exceeds a threshold number.

5. The medical system of claim 4, wherein the communication circuitry is further configured to transmit data comprising an indication of a detection of a non-AT episode based on satisfaction of the first criterion and the second criterion.

6. The medical system of claim 1, wherein at least one of the first set or the second set of AT detection criteria comprises a criterion of change in ventricular rate.

7. The medical system of claim 6, wherein the change in ventricular rate criterion comprises a threshold that is a difference value between median time values of a pre-determined number of heart beat intervals before a specific heart beat interval and a pre-determined number of heart beat intervals after the specific heart beat interval.

8. The medical system of claim 1, wherein the first set of AT detection criteria comprises a criterion setting a particular level of regularity for the heart beat intervals over the pre-determined time period.

9. The medical system of claim 1, wherein the second set of AT detection criteria comprises a criterion that at least a first threshold of the heart beat intervals satisfies a second threshold, wherein the first threshold comprises a number or a proportion of the heart beat intervals, wherein the second threshold comprises a particular time value for the heart beat intervals.

10. The medical system of claim 1, wherein the second set of AT detection criteria comprises a criterion that a difference between time values of an interquartile range (IQR) before a specific heart beat interval and an IQR after the specific heart beat interval exceeds a threshold, wherein the IQR corresponding to a configurable range of heart beat intervals.

11. A non-transitory computer-readable storage medium comprising program instructions that, when executed by processing circuitry of a medical system, cause the processing circuitry to:
receive cardiac activity data including heart beat intervals, the cardiac activity data including at least one of electrogram (EGM) data or electrocardiogram (ECG) data;
determine an evidence level of an atrial tachycardia (AT) episode of the patient based on the heart beat intervals in the cardiac activity data;

determine the evidence level indicates relatively regular heart beat intervals in response to the evidence level corresponding to relatively regular heart beat intervals;

determine the evidence level indicates relatively irregular heart beat intervals in response to the evidence level corresponding to relatively irregular heart beat intervals;

based on the determination that the evidence level indicates relatively regular heart beat intervals:

apply, to the cardiac activity data, a first set of AT detection criteria; and indicate a detection of the AT episode based on satisfaction of at least one of the first set of AT detection criteria;

based on the determination that the evidence level indicates relatively irregular heart beat intervals:

apply, to the cardiac activity data, a second set of AT detection criteria, the second set of AT detection criteria including at least one criterion different from the first set of AT detection criteria; and indicate a detection of the AT episode based on satisfaction of at least one of the second set of AT detection criteria; and control communication circuitry to transmit data comprising an indication of the detection of the AT episode to a computing device.

\* \* \* \* \*